(12) United States Patent
Hieftje et al.

(10) Patent No.: US 7,893,408 B2
(45) Date of Patent: Feb. 22, 2011

(54) METHODS AND APPARATUS FOR IONIZATION AND DESORPTION USING A GLOW DISCHARGE

(75) Inventors: Gary M. Hieftje, Bloomington, IN (US); Steven J. Ray, Bloomington, IN (US); Francisco J. Andrade, Leeds (GB); William C. Wetzel, Villa Hills, KY (US); Michael R. Webb, Wilmington, NC (US); Gerardo Gamez, Thun (CH); Jacob T. Shelley, Bloomington, IN (US)

(73) Assignee: Indiana University Research and Technology Corporation, Indianapolis, IN (US)

( * ) Notice: Subject to any disclaimer, the term of this patent is extended or adjusted under 35 U.S.C. 154(b) by 298 days.

(21) Appl. No.: 11/980,843

(22) Filed: Oct. 31, 2007

(65) Prior Publication Data

US 2008/0202915 A1 Aug. 28, 2008

Related U.S. Application Data

(60) Provisional application No. 60/856,129, filed on Nov. 2, 2006.

(51) Int. Cl.
*H05H 1/26* (2006.01)
(52) U.S. Cl. .................. 250/423 R; 250/424; 250/425; 250/426; 250/288; 436/153; 313/619
(58) Field of Classification Search .................. 250/281, 250/282, 288, 423 R, 424, 425, 426; 436/153; 313/619
See application file for complete search history.

(56) References Cited

U.S. PATENT DOCUMENTS

| | | | | |
|---|---|---|---|---|
| 5,184,016 A | * | 2/1993 | Ronan et al. ................ | 250/288 |
| 5,192,865 A | * | 3/1993 | Zhu ........................... | 250/288 |
| 5,889,404 A | * | 3/1999 | Abdel-Rahman et al. ... | 324/464 |
| 6,661,178 B1 | * | 12/2003 | Bertrand et al. ........ | 315/111.91 |
| 6,949,741 B2 | * | 9/2005 | Cody et al. ................. | 250/288 |
| 7,112,785 B2 | * | 9/2006 | Laramee et al. ............. | 250/288 |
| 7,525,086 B2 | * | 4/2009 | Suzuki ....................... | 250/288 |
| 7,544,933 B2 | * | 6/2009 | Cooks et al. ................ | 250/288 |
| 7,586,092 B1 | * | 9/2009 | Karpetsky .................... | 250/288 |
| 2005/0115361 A1 | * | 6/2005 | Forbes Jones et al. ........ | 75/336 |
| 2005/0230635 A1 | * | 10/2005 | Takats et al. ................ | 250/424 |
| 2009/0121638 A1 | * | 5/2009 | Price et al. ............. | 315/111.21 |

OTHER PUBLICATIONS

Millard, et al ("Diode laser absorption measurements of metastable helium in glow discharges" Plasma Sources Sci. Technol vol. 7 No. 389, 1998).*

(Continued)

*Primary Examiner*—Jack I Berman
*Assistant Examiner*—Michael Maskell
(74) *Attorney, Agent, or Firm*—Barnes & Thornburg LLP

(57) ABSTRACT

A method for ionizing and desorbing a sample for analysis includes energizing a first and second electrode to produce a glow discharge at atmospheric pressure. The method further includes supplying a carrier gas to at least a portion of the glow discharge to create effluents thereof. The method further includes conducting the effluents of the glow discharge to the sample to ionize and desorb the sample for analysis. An associated apparatus is also disclosed.

17 Claims, 21 Drawing Sheets
(2 of 21 Drawing Sheet(s) Filed in Color)

OTHER PUBLICATIONS

Anderson, C., M. Hur, P. Zhang, L. Mangolini, and U. Kortshagen, "Two-Dimensional Space-Time-Resolved Emission Spectroscopy on Atmospheric Pressure Glows in Helium with Impurities", Journal of Applied Physics, vol. 96, No. 4, 2004, pp. 1835-1839.

Andrade, F. J., W. C. Wetzel, G. C. Y. Chan, M. R. Webb, G. Gamez, S. J. Ray, G. M. Hieftje, "A New, Versatile, Direct-Current Helium Atmospheric-Pressure Glow Discharge", Journal of Analytical Atomic Spectrometry, vol. 21, 2006, pp. 1175-1184.

Boyle, W. S., and F. E. Haworth, "Glow-To-Arc Transition", Physical Review, vol. 101, No. 3, 1956, pp. 935-938.

Brewer, T. M., J. Castro, and R. K. Marcus, "Particle Beam Sample Introduction into Glow Discharge Plasmas for Speciation Analysis", Spectrochimica Acta Part B, vol. 61, 2006, pp. 134-149.

Bruins, A. P., "Atmospheric-Pressure-Ionization Mass Spectrometry", Trends in Analytical Chemistry, vol. 13, No. 1, 1994, pp. 37-43.

Bystroff, R. I., L. R. Layman, and G. M. Hieftje, "Investigation into the Operating Characteristics of a "Microarc" Atmospheric-Pressure Glow Discharge", Applied Spectroscopy, vol. 33, No. 3, 1979, pp. 230-240.

Carroll, D. I., I. Dzidic, R. N. Stillwell, K. D. Haegele, and E. C. Horning, "Atmospheric Pressure Ionization Mass Spectrometry: Corona Discharge Ion Source for Use in Liquid Chromatograph-Mass Spectrometer-Computer Analytical System", Analytical Chemistry, vol. 47, No. 14, 1975, pp. 2369-2373.

Chen, H., N. N. Talaty, Z. Takats, and R. G. Cooks, "Desorption Electrospray Ionization Mass Spectrometry for High-Throughput Analysis of Pharmaceutical Samples in the Ambient Environment", Anal. Chem., vol. 77, No. 21, 2005, pp. 6915-6927.

Cody, R. B., J. A. Laramee, and H. D. Durst, "Versatile New Ion Source for the Analysis of Materials in Open Air Under Ambient Conditions", Anal. Chem. vol. 77, No. 8, 2005, pp. 2297-2302.

Collins, C. B., and W. W. Robertson, "Spectra Excited in a Helium Afterglow", The Journal of Chemical Physics, vol. 40, No. 3, 1964, pp. 701-712.

Conrads, H., and M. Schmidt, "Plasma Generation and Plasma Sources", Plasma Sources Sci. Technol., vol. 9, 2000, pp. 441-454.

Cooks, R. G., Z. Ouyang, Z. Takats, J. M. Wiseman, "Ambient Mass Spectrometry", Science, vol. 311, 2006, pp. 1566-1570.

Cotte-Rodriguez, I., and R. G. Cooks, "Non-Proximate Detection of Explosives and Chemical Warfare Agent Simulants by Desorption Electrospray Ionization Mass Spectrometry", Chem. Commun, 2006, pp. 2968-2970.

Dothan, F., and Y. M. Kagan, "Composition of the Positive Column of a Helium Glow Discharge at Intermediate Pressures", J. Phys. D: Appl. Phys., vol. 12, 1979, pp. 2155-2166.

Ennis, C. J., J. C. Reynolds, B. J. Keely, L. J. Carpenter, "A Hollow Cathode Proton Transfer Reaction Time of Flight Mass Spectrometer", International Journal of Mass Spectrometry, vol. 247, 2005, pp. 72-80.

Franzke, J., K. Kunze, M. Miclea, and K. Niemax, "Microplasmas for Analytical Spectrometry", J. Anal. At. Spectrom., vol. 18, 2003, pp. 802-807.

Golubovskii, Y. B., V. A. Maiorov, J. Behnke, and J. F. Behnke, "Modelling of the Homogeneous Barrier Discharge in Helium at Atmospheric Pressure", Journal of Physics D: Applied Physics, vol. 36, 2003, pp. 39-49.

Good, A., D. A. Durden, and P. Kebarle, "Mechanism and Rate Constants of Ion-Molecule Reactions Leading to Formation of $H^+(H_2O)_n$ in Moist Oxygen and Air", Journal of Chemical Physics, vol. 52, No. 1, 1970, pp. 222-229.

Guevremont, R. and R. E. Sturgeon, "Atmospheric Pressure Helium RF Plasma Source for Atomic and Molecular Mass Spectrometry", J. Anal. At. Spectrom, vol. 15, 2000, pp. 37-42.

Guzowski Jr., J. P, and G. M. Hieftje, "Characterization of Switched Direct Current Gas Sampling Glow Discharge Ionization Source for the Time-Of-Flight Mass Spectrometer", J. Anal. At. Spectrom, vol. 15, 2000, pp. 27-36.

Hansel, A., A. Jordan, C. Warneke, R. Holzinger, A. Wisthaler, and W. Lindinger, "Proton-Transfer-Reaction Mass Spectrometry (PTR-MS): On-Line Monitoring of Volatile Organic Compounds at Volume Mixing Ratios of a Few pptv", Plasma Sources Sci. Technol., vol. 8, 1999, pp. 332-336.

Hansel, A., A. Jordan, R. Holzinger, P. Prazeller, W. Vogel, and W. Lindinger, "Proton Transfer Reaction Mass Spectrometry: On-Line Trace Gas Analysis at the ppb Level", International Journal of Mass Spectrometry and Ion Processes, vol. 149/150, 1995, pp. 609-619.

Haug, B., H. Morgner, and V. Staemmler, "Experimental and Theoretical Study of Penning Ionisation of $H_2O$ by Metastable Helium $He(2^3S)$", J. Phys, B: At. Mol. Phys., vol. 18, 1985, pp. 259-274.

Houk, R. S., and Y. Zhai, "Comparison of Mass Spectrometric and Optical Measurements of Temperature and Electron Density in the Inductively Coupled Plasma During Mass Spectrometric Sampling", Spectrochimica Acta Part B, vol. 56, 2001, pp. 1055-1067.

Ichikawa, Y., and S. Teii, "Molecular Ion and Metastable Atom Formations and Their Effects on the Electron Temperature in Medium-Pressure Rare-Gas Positive-Column Plasmas", J. Phys. D: Appl. Phys., vol. 13, 1980, pp. 2031-2043.

Kanazawa, S., M. Kogoma, T. Moriwaki, and S. Okazaki, "Stable Glow Plasma at Atmospheric Pressure", J. Phys. D: Appl. Phys., vol. 21, 1988, pp. 838-840.

Kauppila, T. J., J. M. Wiseman, R. A. Ketola, T. Kotiaho, R. G. Cooks and R. Kostiainen, "Desorption Electrospray Ionization Mass Spectrometry for the Analysis of Pharmaceuticals and Metabolites", Rapid Commun. Mass Spectrom., vol. 20, 2006, pp. 387-392.

Karanassios, V., "Microplasmas for Chemical Analysis: Analytical Tools or Research Toys?", Spectrochimica Acta Part B, vol. 59, 2004, pp. 909-928.

Kebarle, P., S. K. Searles, A. Zolla, J. Scarborough, and M. Arshadi, "The Solvation of the Hydrogen Ion by Water Molecules in the Gas Phase. Heats and Entropies of Solvation of Individual Reactions: $H^+(H_2O)_{n-1}+H_2O \rightarrow H^+(H_2O)_n$", Journal of Mass Spectrometry, vol. 32, 1997, pp. 915-921.

Kutasi, K., P. Hartmann, and Z. Donko, "Self-Consistent Modelling of Helium Discharges: Investigation of the Role of $He_2^+$ ions", J. Phys D: Appl. Phys, vol. 34, 2001, p. 3368-3377.

Lawler, J. E., "Experimental and Theoretical Investigation of the Optogalvanic Effect in the Helium Positive Column", Physical Review A, vol. 22, No. 3, 1980, pp. 1025-1033.

Lawler, J. E., and U. Kortshagen, "Self-Consistent Monte Carlo Simulations of the Positive Column of Gas Discharges", J. Phys. D: Appl. Phys., vol. 32, 1999, pp. 3188-3198.

Layman, L. R. and G. M. Hieftje, "New, Computer-Controlled Microwave Discharge Emission Spectrometer Employing Microarc Sample Atomization for Trace and Micro Elemental Analysis", Analytical Chemistry, vol. 47, No. 2, 1975, pp. 194-202.

Lewis, C. L., M. A. Moser, W. Hang, D. E. Dale, Jr., D. C. Hassell, V. Majidi, "Influence of Discharge Parameters on Real-Time Chemical Speciation for Gas Chromatography Pulsed Glow Discharge Plasma Time-of-Flight Mass Spectrometry", J. Anal. At. Spectrom., vol. 18, 2003, pp. 629-636.

Lewis, C. L., M. A. Moser, D. E. Dale, Jr., W. Hang, C. Hassell, F. L. King, and V. Majidi, "Time-Gated Pulsed Glow Discharge: Real-Time Chemical Speciation at the Elemental, Structural, and Molecular Level for Gas Chromatography Time-of-Flight Mass Spectrometry", Analytical Chemistry, vol. 75, No. 9, 2003, pp. 1983-1996.

Majidi, V., M. Moser, C. Lewis, W. Hang, and F. L. King, "Explicit Chemical Speciation by Microsecond Pulsed Glow Discharge Time-of-Flight Mass Spectrometry: Concurrent Acquisition of Structural, Molecular and Elemental Information", J. Anal. At. Spectrom., vol. 15, 2000, pp. 19-25.

Mangolini L., C. Anderson, J. Heberlein, and U. Kortshagen, "Effects of Current Limitation Through the Dielectric in Atmospheric Pressure Glows in Helium", J. Phys. D: Appl. Phys., vol. 37, 2004, pp. 1021-1030.

Mangolini, L., K. Orlov, U. Kortshagen, J. Heberlein, and U. Kogelschatz, "Radial Structure of a Low-Frequency Atmospheric-Pressure Glow Discharge in Helium", Applied Physics Letters, vol. 80, No. 10, 2002, pp. 1722-1724.

Marcus, R. K., E. H. Evans, and J. A. Caruso, "Tunable Plasma Sources in Analytical Spectroscopy: Current Status and Projections", J. Anal. At. Spectrom, vol. 15, 2000, pp. 1-5.

Mason, R., and D. Milton, "Glow Discharge Mass Spectrometry of Some Organic Compounds", International Journal of Mass Spectrometry and Ion Processes, vol. 91, 1989, pp. 209-225.

Massines, F., A. Rabehi, P. Decomps, R. B. Gadri, P. Segur, and C. Mayoux, "Experimental and Theoretical Study of a Glow Discharge at Atmospheric Pressure Controlled by Dielectric Barrier", Journal of Applied Physics, vol. 83, No. 6, 1998, pp. 2950-2957.

McLuckey, S. A., G. L. Glish, K. G. Asano, and B. C. Grant, "Atmospheric Sampling Glow Discharge Ionization Source for the Determination of Trace Organic Compounds in Ambient Air", Anal. Chem. vol. 60, 1988, pp. 2220-2227.

Mezei, P., T. Cserfalvi, and M. Janossy, "On the Pressure Dependence of the Positive Column Cross Section in High-Pressure Glow Discharges", J. Phys. D: Appl. Phys., vol. 34, 2001, pp. 1914-1918.

Mezei, P., T. Cserfalvi, M. Janossy, K. Szocs, and H. J. Kim, "Similarity Laws for Glow Discharges with Cathodes of Metal and an Electrolyte", J. Phys, D: Appl. Phys., vol. 31, 1998, pp. 2818-2825.

Nersisyan, G., T. Morrow, and W. G. Graham, "Measurements of Helium Metastable Density in an Atmospheric Pressure Glow Discharge", Applied Physics Letters, vol. 85, No. 9, 2004, pp. 1487-1489.

Newman, K., and R. S. Mason, "Gas Chromatography Combined with Fast Flow Glow Discharge Mass Spectrometry (GC-FFGD-MS)", J. Anal. At. Spectrom., vol. 19, 2004, pp. 1134-1140.

Newman, K., and R. S. Mason, "Organotin Speciation Using Fast Flow Glow Discharge Mass Spectrometry", J. Anal. At. Spectrom., vol. 20, 2005, pp. 830-838.

Nicol, G., J. Sunner, and P. Kebarle, "Kinetics and Thermodynamics of Protonation Reactions: $H_3O^+ (H_2O)_n + B = BH^+ (H_2O)_b + (h-b+1) H_2O$, Where B is a Nitrogen, Oxygen or Carbon Base", International Journal of Mass Spectrometry and Ion Processes, vol. 84, 1988, pp. 135-155.

Okazaki, S., M. Kogoma, M. Uehara, and Y. Kimura, "Appearance of Stable Glow Discharge in Air, Argon, Oxygen and Nitrogen at Atmospheric Pressure Using a 50 Hz Source", J. Phys. D: Appl. Phys, vol. 26, 1993, pp. 889-892.

Popov, I. A., H. Chen, O. N. Kharybin, E. N. Nikolaev, and R. G. Cooks, "Detection of Explosives on Solid Surfaces by Thermal Desorption and Ambient Ion/Molecule Reactions", Chem. Commun., 2005, pp. 1953-1955.

Sofer, I., J. Zhu, H. S. Lee, W. Antos, and D. M. Lubman, "An Atmospheric-Pressure Glow Discharge Ionization Source", Applied Spectroscopy, vol. 44, No. 8, 1990, pp. 1391-1398.

Staack, D., B. Farouk, A. Gutsol, and A. Fridman, "Characterization of a DC Atmospheric Pressure Normal Glow Discharge", Plasma Sources Sci. Technol., vol. 14, 2005, pp. 700-711.

Stark, R. H., and K. H. Schoenbach, "Direct Current Glow Discharges in Atmospheric Air", Applied Physics Letters, vol. 74, No. 25, 1999, pp. 3770-3772.

Stark, R. H., and K. H. Schoenbach, "Direct Current High-Pressure Glow Discharges", Journal of Applied Physics, vol. 85, No. 4, 1999, pp. 2075-2080.

Steiner, R. E., C. L. Lewis, and V. Majidi, "Consideration of a Millisecond Pulsed Glow Discharge Time-of-Flight Mass Spectrometer for Concurrent Elemental and Molecular Analysis", J. Anal. At. Spectrom, vol. 14, 1999, pp. 1537-1541.

Stevefelt, J., J. M. Pouvesle, and A. Bouchoule, "Reaction Kinetics of a High Pressure Helium Fast Discharge Afterglow", J. Chem. Phys., vol. 76, No. 8, 1982, pp. 4006-4015.

Sunner, J., G. Nicol, and P. Kebarle, "Factors Determining Relative Sensitivity of Analytes in Positive Mode Atmospheric Pressure Ionization Mass Spectrometry", Anal. Chem. vol. 60, 1988, pp. 1300-1307.

Takats, Z., J. M. Wiseman, and R. G. Cooks, "Ambient Mass Spectrometry Using Desorption Electrospray Ionization (DESI): Instrumentation, Mechanisms and Applications in Forensics, Chemistry, and Biology", J. Mass Spectrom, vol. 40, 2005, pp. 1261-1275.

Takats, Z., I. Cotte-Rodriguez, N. Talaty, H. Chen, and R. G. Cooks, "Direct, Trace Level Detection of Explosives on Ambient Surfaces by Desorption Electrospray Ionization Mass Spectrometry", Chem. Commun, 2005, pp. 1950-1952.

Takats, Z., J. M. Wiseman, B. Gologan, and R. G. Cooks, "Mass Spectrometry Sampling Under Ambient Conditions with Desorption Electrospray Ionization", Science, vol. 306, 2004, pp. 471-473.

Talaty, N., Z. Takats, and R. G. Cooks, "Rapid in Situ Detection of Alkaloids in Plant Tissue Under Ambient Conditions Using Desorption Electrospray Ionization", Analyst, vol. 130, 2005, pp. 1624-1633.

Van de Sande, M. J., P. van Eck, A. Sola, A. Gamero, J. J. A. M. van der Mullen, "Entrainment of Ambient Air into a Spectrochemical Inductively Coupled Argon Plasma", Spectrochimica Acta Part B, vol. 58, 2003, pp. 457-467.

Wagatsuma, K. and K. Hirokawa, "High Sensitivity Measurement of Atomic Emission Spectra with an Applied Voltage Modulation Technique", Anal. Chem. vol. 56, 1984, pp. 2732-2735.

Williams, J. P., V. J. Patel, R. Holland, and J. H. Scrivens, "The Use of Recently Described Ionisation Techniques for the Rapid Analysis of Some Common Drugs and Samples of Biological Origin", Rapid Commun. Mass Spectrom, vol. 20, 2006, pp. 1447-1456.

Wiseman, J. M., S. M. Puolitaival, Z. Takats, R. G. Cooks, and R. M. Caprioli, "Mass Spectrometric Profiling of Intact biological Tissue by Using Desorption Electrospray Ionization", Angew. Chem. Int. Ed., vol. 44, 2005, pp. 7094-7097.

Yokoyama, T., M. Kogoma, T. Moriwaki, and S. Okazaki, "The Mechanism of the Stabilisation of Glow Plasma at Atmospheric Pressure", J. Phys, D: Appl. Phys, vol. 23, 1990, pp. 1125-1128.

Fan, H. Y., "The Transition from Glow Discharge to Arc", Physical Review, vol. 55, 1939, pp. 769-775.

Zhao, J., J. Zhu, and D. M. Lubman, "Liquid Sample Injection Using an Atmospheric Pressure Direct Current Glow Discharge Ionization Source", Anal. Chem, vol. 64, 1992, pp. 1426-1433.

Andrade, F. J.; Shelley, J. T.; Wetzel, W. C.; Webb, M. R.; Gamez, G.; Ray, S. J.; Hieftje, G. M., "Atmospheric Pressure Chemical Ionization Source. 1. Ionization of Compounds in the Gas Phase," Analytical Chemistry 2008, vol. 80, No. 8, 2646-2653.

Andrade, F. J.; Shelley, J. T.; Wetzel, W. C.; Webb, M. R.; Gamez, G.; Ray, S. J.; Hieftje, G. M., "Atmospheric Pressure Chemical Ionization Source. 2. Desorption—Ionization for the Direct Analysis of Solid Compounds," Analytical Chemistry 2008, vol. 80, No. 8, 2654-2663.

Barnes, J. H.; Schilling, G. D.; Hieftje, G. M.; Sperline, R. P.; Denton, M. B.; Barinaga, C. J.; Koppenaal, D. W., "Use of a Novel Array Detector for the Direct Analysis of Solid Samples by Laser Ablation Inductively Coupled Plasma Sector-Field Mass Spectrometry," American Society for Mass Spectrometry 2004, vol. 15, 769-776.

Bleiner, D.; Plotnikov, A.; Vogt, C.; Wetzig, K.; Gunther, D., "Depth Profile Analysis of Various Titanium Based Coatings on Steel and Tungsten Carbide Using Laser Ablation Inductively Coupled Plasma—"Time of Flight" Mass Spectrometry," J. Anal Chem 2000, vol. 368, 221-226.

Caprioli, R. M.; Farmer, T. B.; Gile, J., "Molecular Imaging of Biological Samples: Localization of Peptides and Proteins Using MALDI-T of MS," Anal. Chem. 1997, vol. 69, 4751-4760.

Costa, A. B.; Cooks, R. G., "Simulation of Atmospheric Transport and Droplet-Thin Film Collisions in Desorption Electrospray Ionization," Chemical Communications 2007, 3915-3917.

Ifa, D. R.; Gumaelius, L. M.; Eberlin, L. S.; Manicke, N. E.; Cooks, R. G., "Forensic Analysis of Inks by Imaging Desorption Electrospray Ionization (DESI) Mass Spectrometry," Analyst 2007, vol. 132, 461-467.

Klinkert, I.; McDonnell, L. A.; Luxembourg, S. L.; Altelaar, A. F. M.; Amstalden, E. R.; Piersma, S. R.; Heeren, R. M. A., "Tools and strategies for visualization of large image data sets in high-resolution imaging mass spectrometry," Rev. Sci. Instrum. 2007, vol. 78, 053716-1-053716-10.

Li, Y.; Shrestha, B.; Vertes, A., "Atmospheric Pressure Molecular Imaging by Infrared MALDI Mass Spectrometry," Anal. Chem. 2007, vol. 79, 523-532.

Luxembourg, S. L.; Mize, T. H.; McDonnell, L. A.; Heeren, R. M. A., "High-Spatial Resolution Mass Spectrometric Imaging of Peptide and protein Distributions on a Surface," Anal. Chem., 2004, vol. 76, 5339-5344.

McDonnell, L. A., Heeren, R. M. A, "Imaging Mass Spectrometry," Mass Spectrom. Rev. 2007, vol. 26, 606-643.

Na, N.; Zhao, M. X.; Zhang, S.; Yang, C.; Zhang, X., "Development of a Dielectric Barrier Discharge Ion Source for Ambient Mass Spectrometry," J. Am. Soc. Mass. Spectrom. 2007, vol. 18, 1859-1862.

Nemes, P.; Vertes, A., "Laser Ablation Electrospray Ionization for Atmospheric Pressure, in Vivo, and Imaging Mass Spectrometry," Anal. Chem. 2007, vol. 79, 8098-8106.

Ratcliffe, L. V.; Rutten, F. J. M.; Barrett, D. A.; Whitmore, T.; Seymour, D.; Greenwood, C.; Aranda-Gonzalvo, Y.; Robinson, S.; McCoustra, M., "Surface Analysis Under Ambient Conditions Using Plasma-Assisted Desorption/Ionization Mass Spectrometry," Anal. Chem. 2007, vol. 79, 6094-6101.

Venter, A.; Sojka, P. E.; Cooks, R. G., "Droplet Dynamics and Ionization Mechanisms in Desorption Electrospray Ionization Mass Spectrometry," Anal. Chem. 2006, vol. 78, 8549-8555.

Wiseman, J. M.; Ifa, D. R.; Song, Q.; Cooks, R. G., "Tissue Imaging at Atmospheric Pressure Using Desorption Electrospray Ionization (DESI) Mass Spectrometry," Angewandte Chemie-International Edition 2006, vol. 45, 7188-7192.

\* cited by examiner

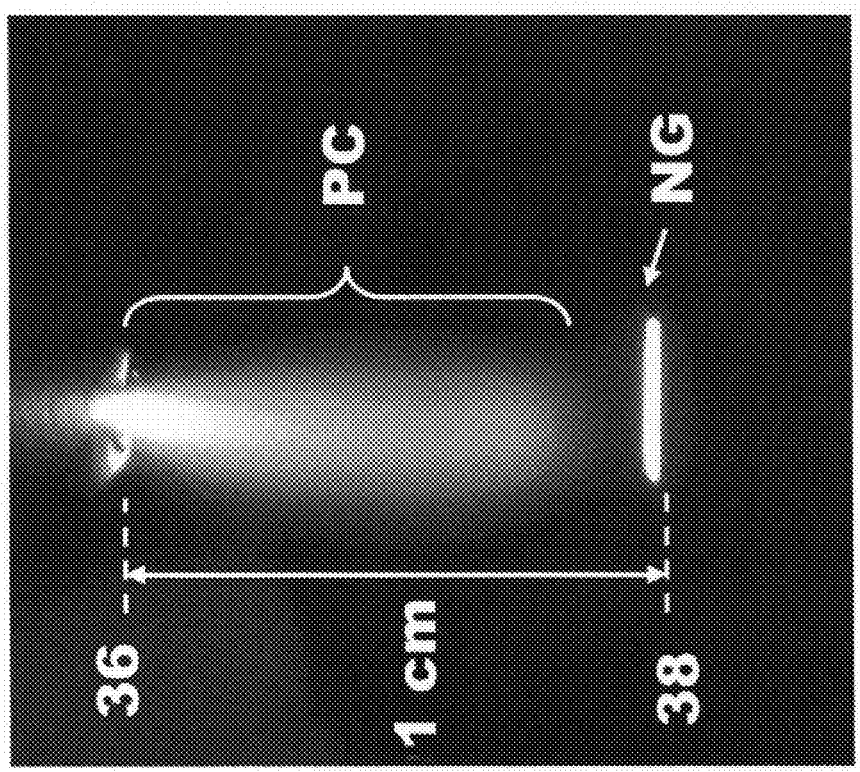

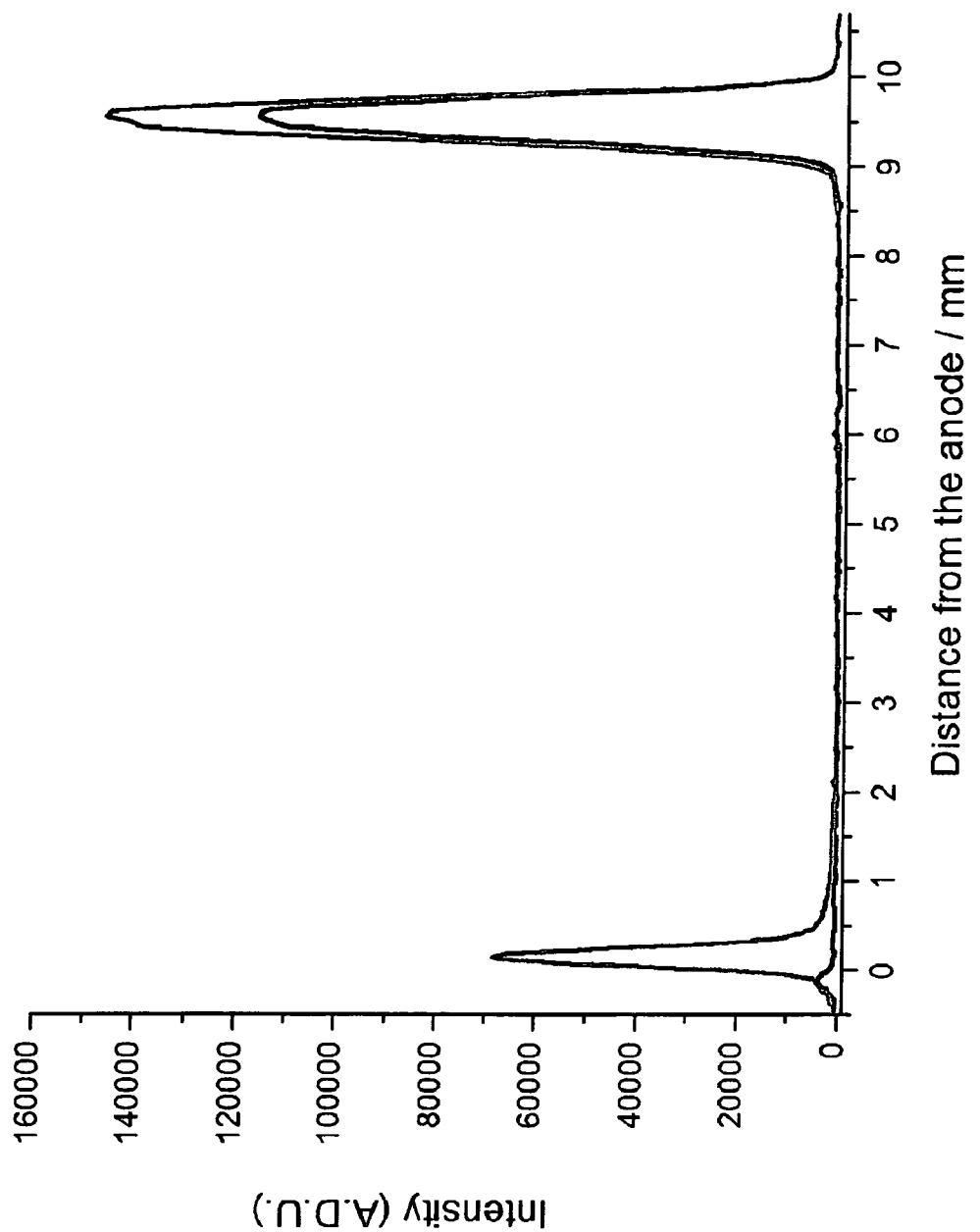

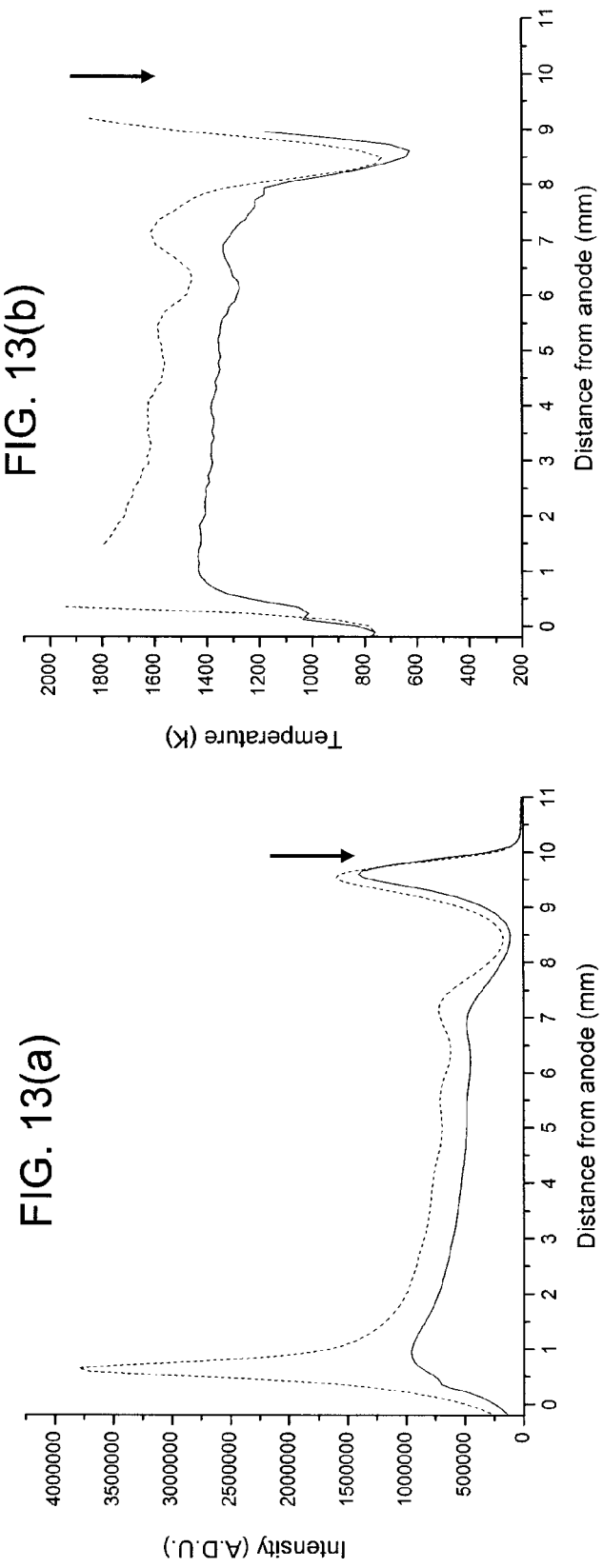

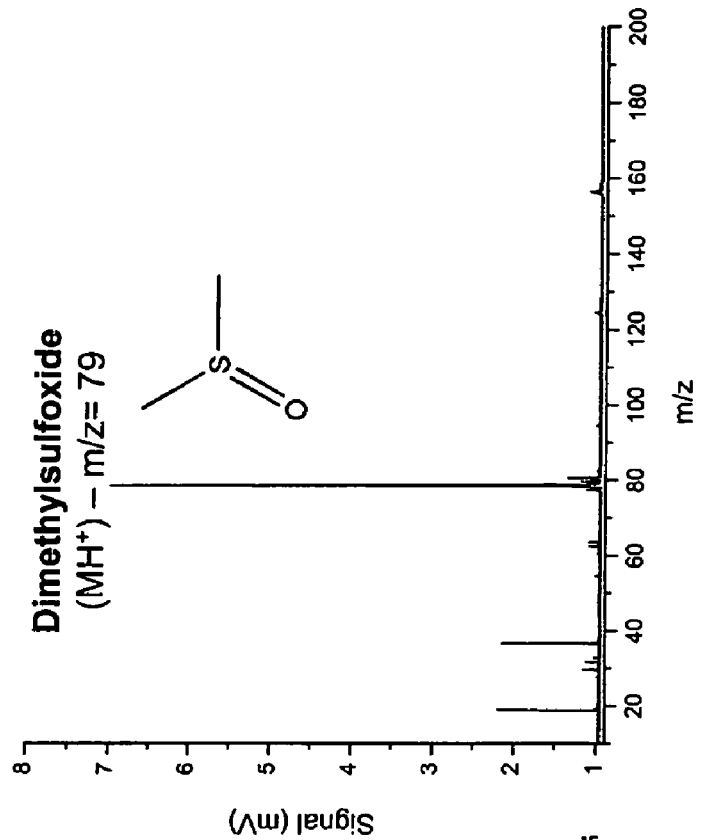
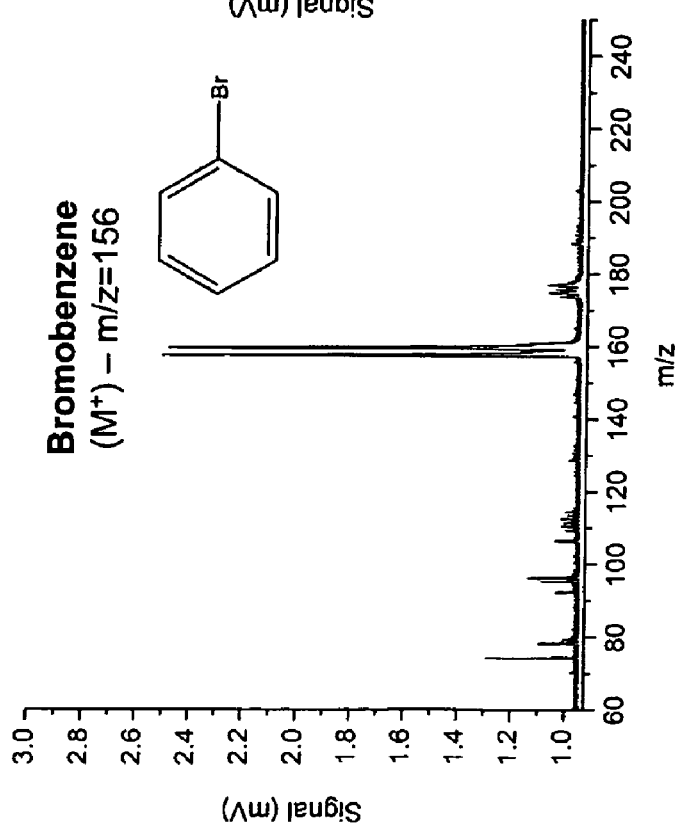
Fig. 14(d)
Fig. 14(c)

| Operating current | 25 mA |
| Helium flow | 0.85 lpm |
| Front plate potential | 35 V |
| Anode potential | 50 V |
| Cathode potential | 500 V |

FIG. 18

| Compound | Main ion signal |
|---|---|
| Alcohols (methanol, ethanol, propanol, butanol, octanol, phenol)<br>Amines (aniline, piperidine)<br>Ketones (acetone, cyclohexanone, butanone)<br>Ethers (ethyl acetate, propyl acetate)<br>Acids (acetic, propanoic) | $MH^+$ |
| Benzenes and derivatives (mono and dihalogenated benzenes)<br>Nitro-aromatic compounds (nitrotoluene)<br>Polynuclear aromatic hydrocarbons (phenanthrene, naphtalene, pyrene) | $M^+$ |

METHODS AND APPARATUS FOR IONIZATION AND DESORPTION USING A GLOW DISCHARGE

This application claims priority under to U.S. Provisional Application No. 60/856,129 filed Nov. 2, 2006, which is expressly incorporated by reference herein in its entirety.

BACKGROUND

Glow discharges have become invaluable analytical sources for spectrometric applications. Efforts to develop glow discharges that can be sustained at atmospheric pressure have been primarily focused on minimizing the effect of transient instabilities of the electrical field on the surface of the electrodes, either by changing the system geometry or by using alternative powering schemes. Changes to the system geometry are based on similarity laws, which state that the gap between the electrodes must be reduced as the pressure is raised, in order to maintain the stability of the glow regime. At atmospheric pressure, sub-millimeter gaps are typically required, which has led to the development of miniaturized dc glow discharges.

Atmospheric pressure glow discharges can be sustained in a variety of gases, including hydrogen and hydrogen-methane mixtures, oxygen, nitrogen and air. Extensive diagnostic studies on a helium atmospheric-pressure glow discharge have been previously performed, including the determination of the helium metastable concentrations within it, the decay kinetics of excited species in the presence of impurities, and several parameters associated with the cathode fall. Several other studies have described atmospheric-pressure glow discharges of different geometries in air and nitrogen.

SUMMARY

In one aspect of the disclosure, a method for ionizing and desorbing a sample for analysis may include energizing a first and second electrode to produce a glow discharge at atmospheric pressure. The method may further include supplying a carrier gas to at least a portion of the glow discharge to create effluents thereof. The method may further include conducting the effluents of the glow discharge to the sample to ionize and desorb the sample for analysis.

In another aspect of the disclosure, an apparatus for ionizing and desorbing a sample for analysis may include a first electrode and a second electrode spaced apart from the first electrode. The apparatus may further include at least one power supply configured to energize the first and second electrode to create a glow discharge at atmospheric pressure therebetween. The apparatus may further include a supply of carrier gas configured to introduce carrier gas to the glow discharge to create effluents of the carrier gas to ionize and desorb the sample for analysis.

BRIEF DESCRIPTION OF THE FIGURES

The patent or application file contains at least one figure executed in color. Copies of this patent or patent application publication with color figure(s) will be provided by the Office upon request and payment of the necessary fee.

FIG. 6 is a photograph illustrating spatial structure of an atmospheric-pressure glow discharge cell;

FIG. 11(a) shows spatially resolved emission from $N_2^+$ in a helium atmospheric pressure glow discharge at two different discharge currents. An inset plot shows the spatially resolved emission from atomic nitrogen in a helium atmospheric pressure glow discharge at two different discharge currents;

FIG. 13(a) shows spatially resolved emission from OH in a helium atmospheric-pressure glow discharge at two different discharge currents;

FIG. 13(b) shows spatially resolved rotational temperature based on OH in a helium atmospheric-pressure glow discharge at two different discharge currents;

FIGS. 14(a)-(d) shows mass spectra of various vapor-phase compounds;

FIG. 18 is a table of optimized operating conditions of a flowing afterglow helium atmospheric pressure glow discharge; and FIG. 19 is a table including a list of compounds and a type of ion obtained using an atmospheric-pressure glow discharge.

DETAILED DESCRIPTION OF THE FIGURES AND TABLES

Figure 1:
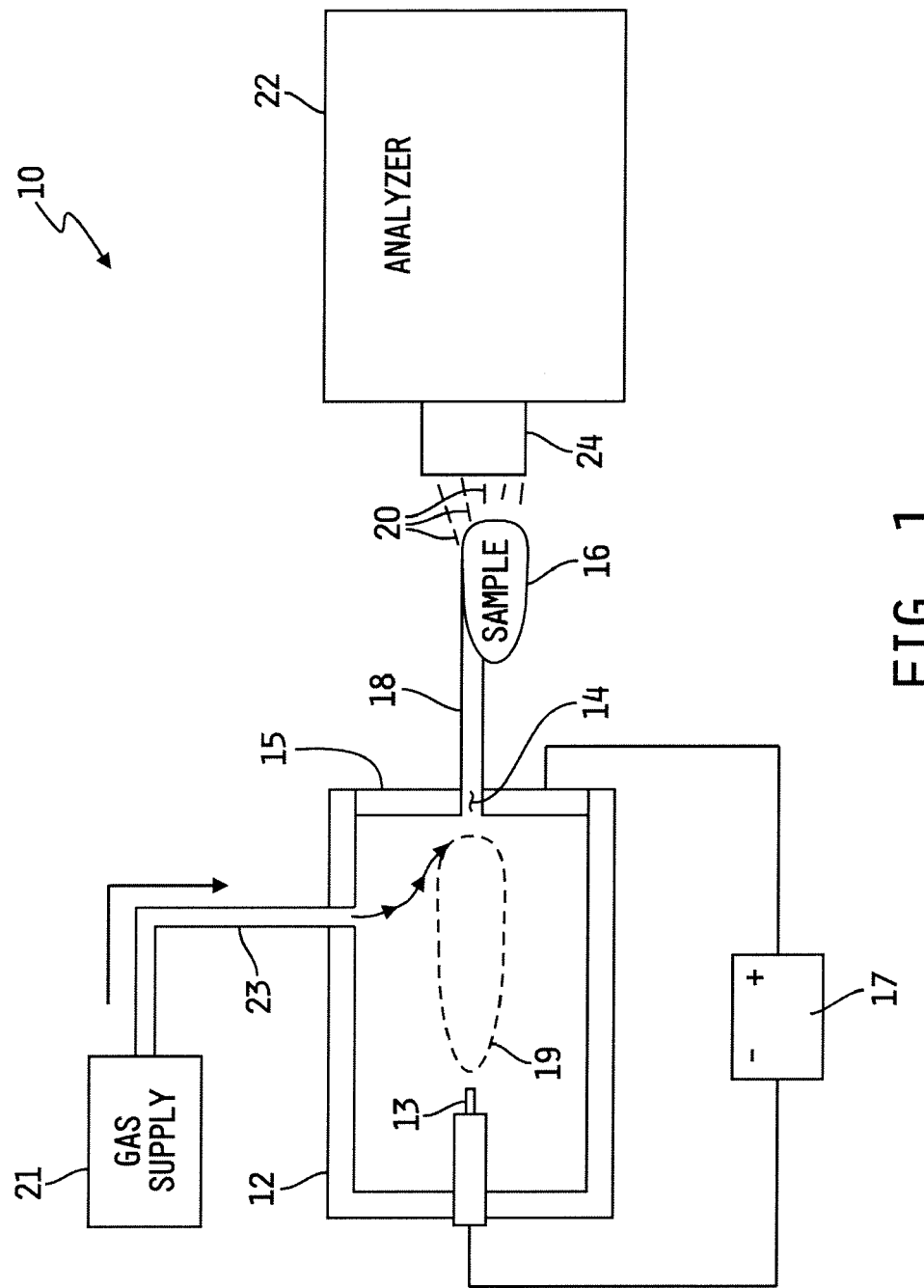
FIG. 1 is a diagrammatic view of a system configured for analyzing a sample prepared with a glow discharge cell.

While the concepts of the present disclosure are susceptible to various modifications and alternative forms, specific illustrative embodiments and methods thereof have been shown by way of example in the drawings and will herein be described in detail. It should be understood, however, that there is no intent to limit the concepts of the present disclosure to the particular forms disclosed, but on the contrary, the intention is to cover all modifications, equivalents, and alternatives falling within the spirit and scope of the invention as defined by the appended claims.

References in the specification to "one embodiment", "an embodiment", "an illustrative embodiment", etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to effect such feature, structure, or characteristic in connection with other embodiments whether or not explicitly described.

Referring now to FIG. 1, a diagrammatic view of an embodiment of a system 10 configured for analyzing a sample 16 is shown. The system 10 includes a glow discharge (GD) cell 12 having an orifice 14 directed towards the sample 16. In one embodiment, the GD cell 12 is operated at atmospheric pressure. As will be further described in detail herein, the GD cell 18 is configured to provide a flowing afterglow 18 to the sample 16, which, through ionization and desorption, provides particles 20 of the sample 16 for analysis by an analyzer 22. The particles 20 may include molecules, molecular fragments, atoms, ions, etc. of the sample 16. FIG. 1 shows a diagrammatic internal view of the GD cell 12, which includes an electrode pin 13 and an electrode plate 15. In one embodiment, a power supply 17 energizes the electrodes 13, 15, such that the electrode pin 13 serves as a cathode and the electrode plate 15 serves as an anode, so as to create an electrical glow discharge 19 in the GD cell 12. In one embodiment, the power supply 17 may be a direct-current high-voltage power supply, such as a Model DRC-5-400R, Universal Voltronics, Mount Kisco, N.Y., for example. The power supply 17 may be operated in various modes for various embodiments, such as current-controlled mode or voltage-controlled mode, for example. Furthermore, it should be appreciated that the polarity of the power supply 17 shown in FIG. 1 may be reversed, such that the electrode pin 13 serves as an anode and the electrode plate 15 serves as a cathode.

A gas supply 21, which in one embodiment may be helium, supplies gas through a supply line 23 into the GD cell 12, as indicated by the arrows. In one embodiment, high-purity helium (99.999% ultra high purity helium, Airgas, Radnor, Pa., for example) may be used. In one embodiment, the helium gas flow was set and monitored by a mass flow controller, such as Model FC-280-SAV, Tylan General, Carson, Calif., for example.

The glow discharge 19 is typically sustained in helium, including other trace impurity atmospheric gases, such that it produces effluents such as ions and excited species, which make up a flowing afterglow 18. The effluents flow to the sample 16 for ionization and desorption thereof, as will be further described herein. Ionized sample particles 20, which may include atoms, molecules, molecular fragments, etc., may enter an inlet 24 of the analyzer 22 for analysis. It should be appreciated that various analyzers 22 may be used such as a time-of-flight mass spectrometer or an ion mobility spectrometer, for example. As will be further described herein, the GD cell 12 may be operated so as to analyze samples of various states, such as gaseous, liquid, and solid.

Figure 2:
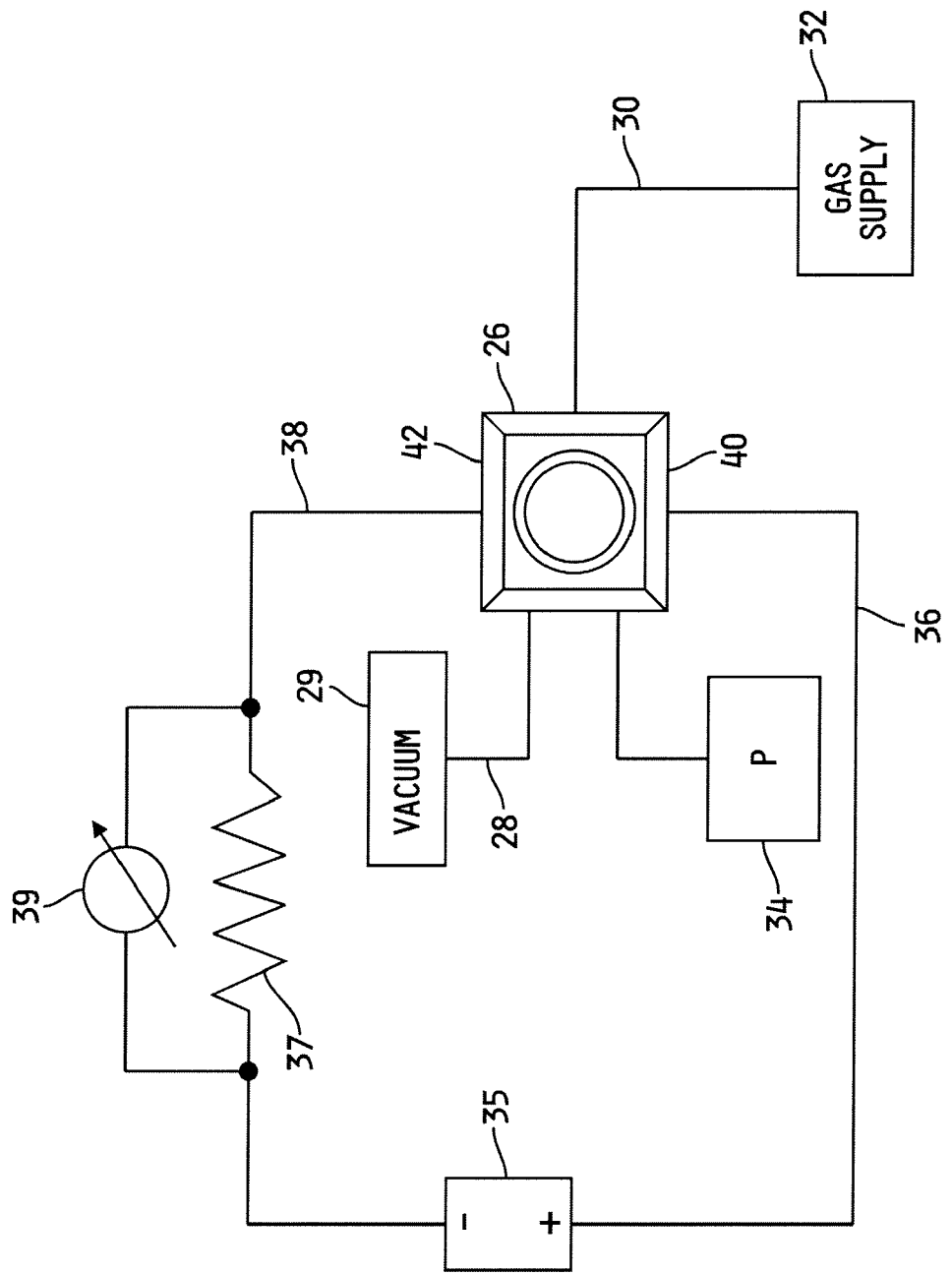
FIG. 2 is a diagrammatic view of an embodiment of a glow discharge cell.

Referring now to FIG. 2, a schematic diagram shows a GD cell 26 configured to determine electrical and spectroscopic characteristics of an electrical discharge created therein. In one embodiment, the GD cell 26 may be a 10-cm cubic aluminum cell used as a discharge chamber for spectroscopic and electrical studies. The GD cell 26 may include openings for a vacuum line 28 of a vacuum 29, a supply line 30 for a gas supply 32, and a pressure monitoring module 34, as shown in FIG. 2. In one embodiment, the vacuum 29 may be a rotary vacuum pump, such as Model RV12, BOC-Edwards, Wilmington, Mass., for example. In one embodiment, the pressure monitoring module 34 may be a capacitance manometer, such as a Baratron, MKS Instruments, Wilmington, Mass., for example. In another embodiment, the pressure monitoring module 34 may be a mechanical vacuum gauge.

In one embodiment, an anode 36 and a cathode 38 may be located on opposite faces 40, 42, respectively, of the GD cell 26 and a view of the electrical discharge was possible by means of a quartz window (not shown). The anode 36 and cathode 38 are connected to a power supply 35. A ballast resistor 37 is connected between the power supply 35 and the cathode 38. A voltmeter 39 is shown connected in parallel to the ballast resistor 27. In one embodiment, all openings in the GD cell 26 were sealed with Viton® o-rings. In embodiments not including the 29 vacuum, the vacuum line 28 may be removed and replaced by a plate fitted with a capillary exit tube.

In one embodiment, the cathode 38 may fabricated from a 3.0-mm diameter pure tungsten rod with a flat, polished end with a 3-mm inner diameter alumina tube (6.35 mm outside diameter) surrounding the cathode 38 serving to limit cathode area. The anode 36 may be a cylindrical 25-mm diameter brass rod with a conical end (half angle ~60°). The shape of the anode 36 increases stability of the electrical discharge in the GD cell 26 in a high pressure (>100 Torr) regime, as will be further discussed herein. The cathode 38 was held in a fixed support (not shown), and the anode 36 was mounted in a threaded base (not shown) to permit adjustment of an inter-electrode gap. The gap, between the cathode 38 and the tip of the anode 36, was always maintained at 1.0 cm, unless otherwise stated.

In one embodiment, spectroscopic measurements were performed by mounting the GD cell 26 in place of an inductively coupled plasma (ICP) torch (not shown) typically used in a commercial ICP emission spectrometer, such as an ACTIVA, Horiba-Jobin Yvon, Longjumeau, Cedex, France, for example. The GD cell 26 was mounted on a movable support to allow its position to be adjusted. The spectral resolution with the ACTIVA particular spectrometer is approximately 8 μm ($\lambda$<430 nm) and 16 μm ($\lambda$>430 nm). The ACTIVA spectrometer provides simultaneous wavelength detection within a chosen spectral window (from approximately 10 nm in the low wavelength range to 3 nm in the visible end of the spectrum). Additionally, by the addition of a cylindrical lens between the front mirror and the entrance slit, improved spatial resolution in the vertical direction was achieved. Spatial resolution of approximately 0.2 mm (2.5 line pairs separated at 50%, 1951 USAF target, group 1-3) was obtained for images of up to 20 mm in size. Therefore, the entire gap between the anode 26 and the cathode 38 could be simultaneously imaged.

In one embodiment, spectroscopic experiments were performed in which the vacuum line 28 to the GD cell 26 was disabled and the GD cell 26 was positioned in an ACTIVA ICP compartment. The anode 36 and cathode 38 were aligned with the ICP torch axis, so the entire inter-electrode gap was focused onto the entrance slit of the spectrometer. In one experiment, UV-Visible spectra were collected over the range 160-800 nm with no spatial discrimination at different integration times in order to verify the absence of self-absorption effects. Subsequently, emission maps of selected spectral regions were generated.

In this experiment, rotational temperature profiles were estimated from emission maps of the Q1-branch of the OH emission. Triplicate spectra were used. Boltzmann plots were linearized and the slope was calculated by the least-squares method. Temperature values with more than 20% RSD or generated from regression lines with a correlation coefficient lower than 0.85 were eliminated.

Figure 3:
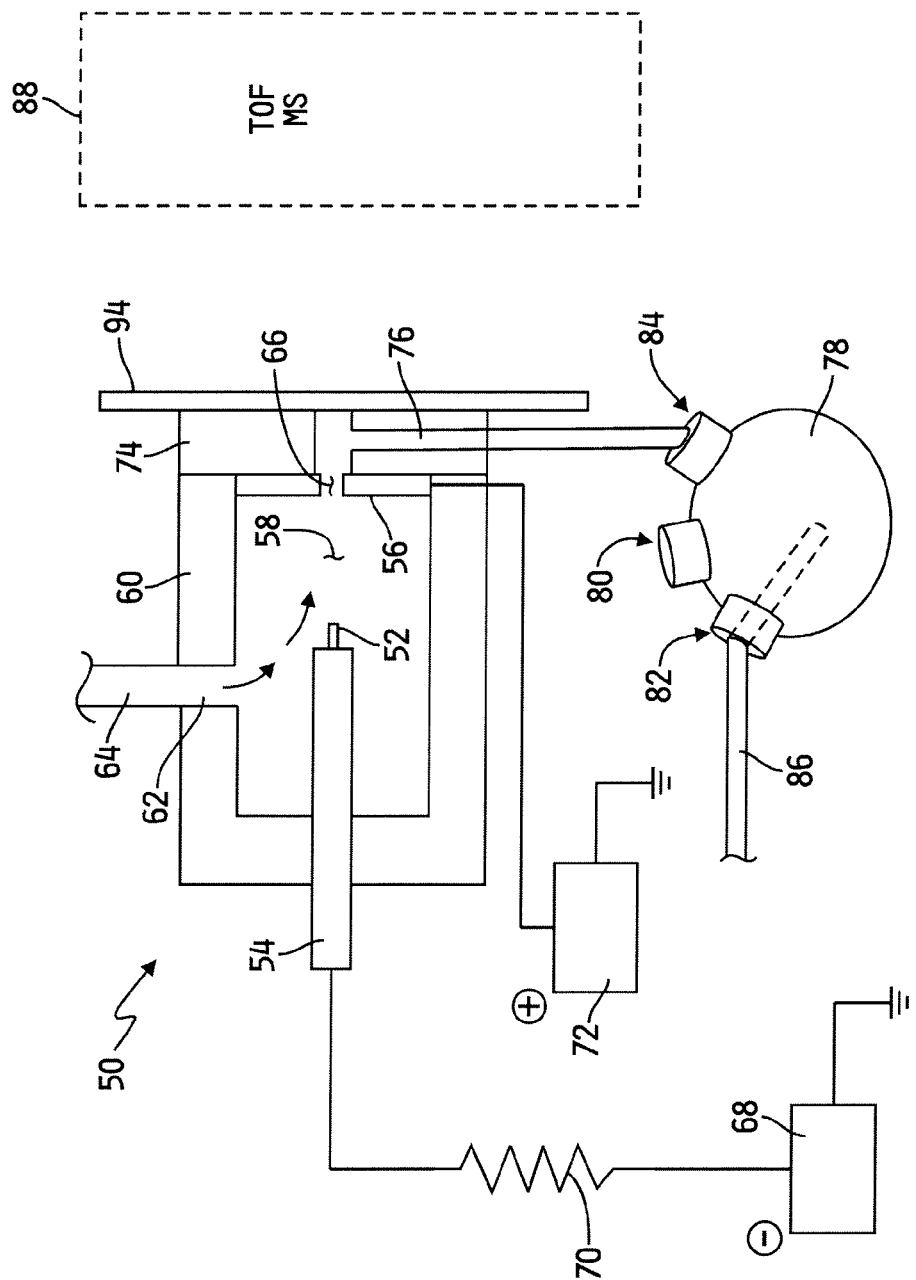
FIG. 3 is a diagrammatic view of another glow discharge cell.
Figure 4:
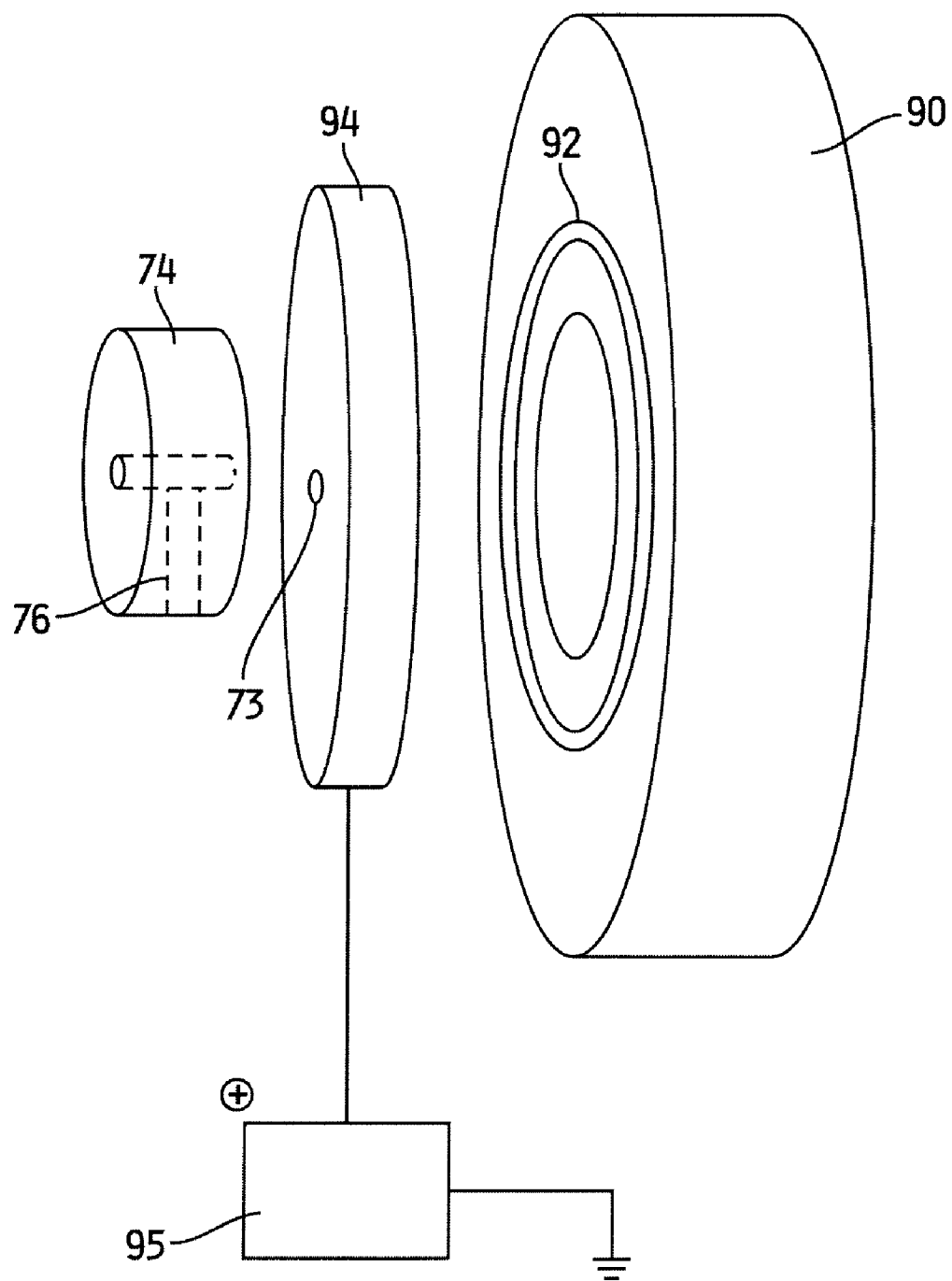
FIG. 4 is a diagrammatic view of a components that may be implemented with the glow discharge cell of FIG. 3.
Figure 5A:
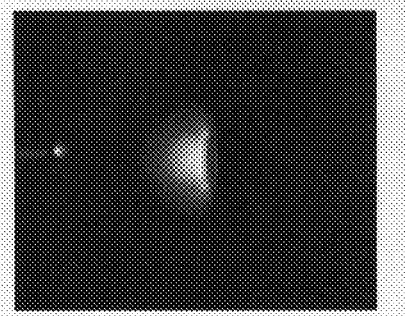
FIGS. 5(a)-5(g) are photographs showing a glow discharge at various pressures.
Figure 5B:
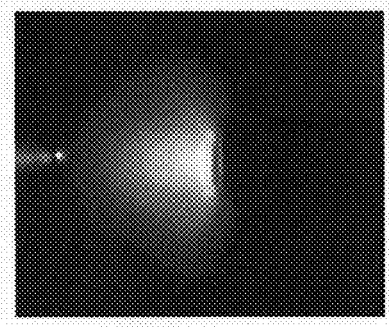
Figure 5C:
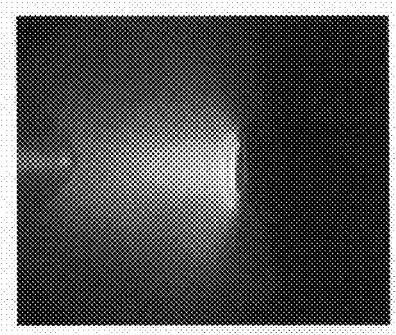
Figure 5D:
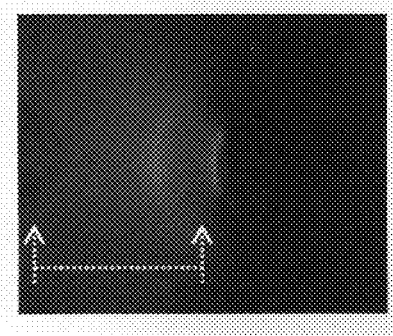
Figure 5E:
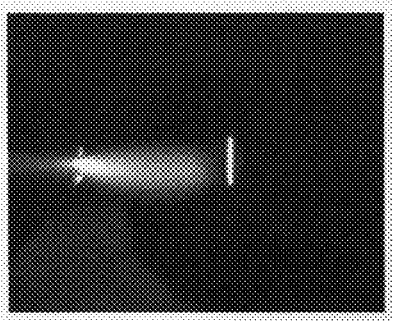
Figure 5F:
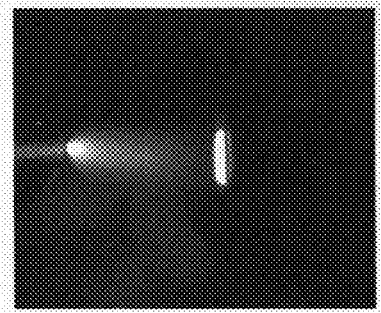
Figure 5G:
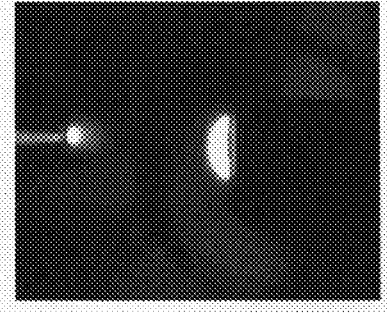

Referring now to FIGS. 3 and 4, a diagrammatic view of a pin-to-plate GD cell 50 used for various spectrometric analyses is shown. In one embodiment, the GD cell 50 is supplied a sample in the form of a gas. It should be appreciated that the embodiments of FIGS. 1-3 may be configured to prepare samples of various states for analysis. In one embodiment, a pin cathode 52 may be made from a tungsten wire (1 mm diameter) mounted in a steel support rod 54. An anode 56 may be a 15-mm diameter, 2-mm thick brass disk with a 1-mm orifice in its center. A gap 58 between anode 56 and cathode 52 may be set at various distances. In illustrative experiments conducted with the GD cell 50, the gap 58 was set at 5 mm.

The cathode 52 and anode 56 were tightly mounted in body 60 formed of Teflon® in this exemplary configuration, which has a suitable entrance 62 for a carrier gas. In illustrative experiments conducted using GD cell 50, the carrier gas used was helium. However, other carrier gases may be used such as argon, for example. The carrier gas is supplied through a supply line 64 from a supply (not shown), similar to that shown in FIG. 1. Carrier gas exits the cell through the orifice 66 in the anode 56. The cathode 52 is connected to a high voltage power supply 68 having a ballast resistor 70 connected thereto. The anode 56 is connected to a low voltage power supply 72. A 5-mm thick disk combiner 74, formed of Teflon® in this exemplary configuration, with a T-channel 76 used for merging an afterglow produced in the GD cell 50 with a sample carrier gas. In an embodiment used for various illustrative experiments described herein, the orifices of the T-channel 76 in the combiner 74 are 1.5 mm diameter.

In one illustrative experiment using the GD cell 50, a sample vapor was introduced through an exponential dilution chamber (EDC) 78 into an afterglow discharge produced by energizing the cathode 52 and anode 56, as shown in FIG. 3. In one embodiment, the EDC may be a 100-mL glass round-bottom flask with a number of openings 80, 82, 84. Opening 80 is used for sample introduction and sealed with a rubber septum. The other two openings 82, 84 may be used for gas input and output, respectively. An additional carrier gas line 86 (independent from the line 64) may be used for transport of sample vapor through the EDC 78. The gas flow through the EDC 78 was regulated by a mass flow controller (not shown) such as a MKS Type 247, MKS Instruments, Wilmington, Mass., for example. The temperature of the EDC 78 was monitored with a thermocouple and was regulated by heating tape connected to a variable autotransformer (not shown). In one illustrative experiment, a sample was injected with a 1 µL syringe, such as a Hamilton syringe, Hamilton, Reno, Nev., for example.

In one embodiment, a time-of-flight (TOF) inductively coupled plasma (ICP) mass spectrometer (MS) 88, shown in phantom, was used in this exemplary configuration for the mass spectrometry experiments, such as a Leco Renaissance® (LECO Corp. St. Joseph, Mich.), for example. In one illustrative experiment, the ICP source was disabled and moved aside, and the GD cell 50 was located facing an ion sampling interface 90 of the spectrometer (not shown), shown in FIG. 4. The ion sampling interface 90 was constructed from a standard Renaissance® sampler whose tip was removed and an o-ring groove 92 was machined onto its front surface. A stainless steel plate 94 may be attached to the interface (and shown attached to combiner 74 in FIG. 3) by plastic screws (not shown), which also allowed proper alignment. However, it should be appreciated that other fasteners may be used. In one embodiment, the plate 94, or front plate, is fitted with a 0.025-mm diameter orifice 73, thus allowing the pressure in the GD cell 50 to remain at proper operating levels (<5 Torr), while open to atmosphere. The plate 94 may be electrically insulated from the rest of the instrument and connected to a low-voltage power supply 95, which allows its electrical potential to be adjusted, as illustrated in FIG. 4.

Referring again to FIG. 2, in illustrative experiments carried out to determine various electrical characteristics in the GD cell 26, the GD cell 26 was evacuated (with no carrier gas flowing) until the pressure reached a value below 0.3 Torr. No leaks were detected. Carrier gas, which in the illustrative experiments described herein was helium, was provided to the GD cell 26, was adjusted to 0.8 l/min and the pressure was regulated by means of a valve (not shown) located in the vacuum line 28. Electrical characteristics of the GD cell 26 were measured as a function of pressure. In particular, current was measured as a function of voltage (at constant pressure) and voltage was determined as a function of pressure (at constant current). Because of the considerably higher voltages required at low pressures, lower currents were used in order to avoid damage of the anode 36 and the cathode 38. In contrast, higher currents were used in the high-pressure range, as will be explained herein.

Images were taken to illustrate the changes in discharge features that were observed at different pressures in the cell 26. In embodiments described herein, a Canon digital camera (Model Rebel XT, Japan) was used to photograph the discharge. Because the brightness of the discharge changes markedly with pressure, the settings of the camera had to be adjusted to avoid saturation. It should be appreciated that the observed colors (described herein) did not correspond exactly with those shown in later figures, likely because of differences between the effective discharge temperature and the color temperature of the CCD in the camera. Additionally, because of the limited dynamic range of commercial cameras and the marked range in intensity of the several regions of the GD cell 26, it is typically difficult to avoid saturation.

The evolution of a gas discharge across the anode 36 and cathode 38 in the presence of helium as the pressure is raised in the GD cell 26 is illustrated by the photographs in FIGS. 5(a)-(g). The arrows in FIG. 5(a) indicated the position of the anode 36 and the cathode 38. At low pressures (<2 Torr) the discharge is sustained at high voltages (approximately 1500 V) and very low currents (below 1 mA) (see FIG. 5(a)). These are higher currents and lower voltages than are ordinarily required to sustain a corona discharge. The low degree of ionization under such conditions is evidenced by the presence of several alternating dark and bright ring-shaped regions around the cathode, an indication that insufficient charges are present to produce a significant distortion of the applied electrical field. When the pressure is increased to 5 Torr (see FIG. 5(b)), however, the operating current rises to the mA range (approximately 2.5 mA), and the applied voltage remains high (approximately 1500 V, the discharge is operated in the current-controlled mode). Visually, the ring-shaped dark regions apparent in FIG. 5(a) shrink towards the surface of the cathode 38 and the negative glow can now be seen as an intense reddish-pink sphere above the cathode 38. The positive column (see FIG. 6) can not be observed. As the pressure is incremented to approximately 100 Torr (FIG. 5(e), 570 V, 30 mA), the easily observed negative glow declines in volume, which leaves a growing space between the negative glow and the anode (the positive column) that shows no emission (FIGS. 5(*c*)-(*d*), approximately 1200 V/10 mA and 790 V and 25 mA, respectively). Only the anode glow is seen as a bright spot.

During the transition between 80 to 100 Torr, a marked change in the characteristics of the discharge can be observed. In this case, the negative glow has become a thick disk at the cathode surface and a region of diffuse orange emission (possibly due to the He (I) 587.6 nm line) appears at the anode end of the positive column. This emission can be seen in FIG. 5(*e*), which in the picture is seen as a faint reddish region close to the anode. As the pressure is raised from 100 to 760 Torr (FIGS. 5(*e*)-(*g*)) most of the changes are observed in the positive column, while the negative glow evolves into a very thin bright layer on the surface of the cathode (FIG. 5(*f*), approximately 640 V and 30 mA). The overall emission from the positive column grows significantly as a very diffuse cylinder having a diameter slightly larger than that of the cathode. Additionally, a bright pink-white emission plume in the positive column is observed to increase in intensity. At the anode surface itself, the positive column collapses into a single bright spot with a faint blue-violet emission around it. The maximum emission intensity of the positive column is located close to the anode. A very well-defined dark region (i.e., the Faraday dark space) separates the positive column from the negative glow (FIG. 5(*g*), 650 V and 30 mA).

The structure described above in connection with FIG. 5(*g*) is characteristic of a glow discharge at atmospheric pressure and may be preserved throughout a wide range of currents and geometrical arrangements. The spatial structure of an atmospheric-pressure glow discharge is shown in FIG. 6, with the anode 36 and the cathode 38 being separated by 1 cm in this embodiment. The negative glow (designated as "NG" in FIG. 6) is typically contained in a thin (sub-mm) layer close to the cathode 38 surface and a large positive column (designated "PC" in FIG. 6) fills the majority of the gap between the anode 36 and the cathode 38. This positive column is diffuse and, depending on the gap between the anode 36 and the cathode 38, has a diameter that can be significantly larger than that of the cathode 38. Because the positive column anchors to the anode 36 at a single spot, a cone-shaped anode was used here to prevent fouling the discharge at high pressures, as opposed to the plate-shaped anode 36 described in regard to the embodiment of FIG. 3. This contraction of the positive column at the anode 36 end, however, must not be confused with the constriction of the positive column characteristic of the glow-to-arc transition. The latter phenomenon generates a positive column having a very thin filamentary structure, and is usually accompanied by a marked increase in electrical conductivity of the discharge. In this illustrative experiment, the glow discharge did not show signs of becoming filamentary.

It should be appreciated that a variety of geometrical arrangements can sustain a glow discharge at atmospheric pressure and the GD cells described herein were chosen for simplicity. In the system shown in FIG. 1, the cathode area (not shown) may be limited by an alumina insulator and, as such, was always completely covered by the discharge. As a result, any changes in the observed current are intrinsically changes in the current density. With this system, gaps between the anode 36 and the cathode 38 up to 4 cm could be employed. In other embodiments, glow discharge cells having gaps up to 12 cm were also tested without compromising the discharge characteristics and stability. Importantly, even at atmospheric pressure, the discharge maintains a diffuse and extremely stable structure. Additionally, the GD cell 26 may be operated for several hours at atmospheric pressure using helium without showing significant changes in the glow or degrading the electrode surfaces. No appreciable erosion or damage of the anode 36 and cathode 38 was be observed even after lengthy periods of operation (~100 hours), which may be the result of the low sputtering capacity of helium.

Voltage stability was evaluated in the illustrative experiments with oscilloscope readings and Fourier power spectra. Discrete frequencies other than 60 Hz (<1%) were not detected in the noise power spectra. However, at high pressures (300-760 Torr), replicates of some experiments yielded a very reproducible current-voltage pattern, but shifted by a constant voltage (usually less than 50V). This shift was attributed to slight differences in the anchoring point of the anode glow, but was not considered relevant for the purposes of this work. Although the discharge might anchor to slightly different points from one experiment to another, it remains fixed at the same point once the anode spot has been established.

FIGS. 7(*a*) and 7(*b*) show current-voltage curves (i vs. V) for the glow discharge cell 26 operated at different ambient pressures. From the positive slopes of the i-V curves obtained at low pressure (FIG. 7(*a*)), it is clear that the GD cell 26 is operating in an abnormal-glow mode, which is consistent with the visual observation of a cathode completely covered by the discharge. Additionally, the slope of this curve drops as the pressure is increased (see inset in FIG. 7(*a*)), which is in agreement with what has been previously found for other reduced-pressure glow discharges. The lower dynamic resistance at higher pressures displayed in FIG. 7(*a*) may be attributed to an increase in the number of ionizing collisions produced by electrons when the density of the medium is higher.

The electrical behavior markedly changes, however, at higher pressures as shown in FIG. 7(*b*). At pressures between 100 to 250 Torr the voltage climbs as the current is raised from 10 to approximately 30 mA, until a maximum voltage of approximately 650 V is reached. Subsequent increases in the operating current do not yield as large a change in voltage. At higher pressures (from 300 Torr up to atmospheric pressure) the voltage is nearly independent of pressure for currents above 50 mA. The dominant pattern in this pressure range is that the slope of the current-voltage curves in the low-current region becomes less as the pressure goes up, because of the higher voltages required to sustain the discharge in the low-current range.

Figure 8:
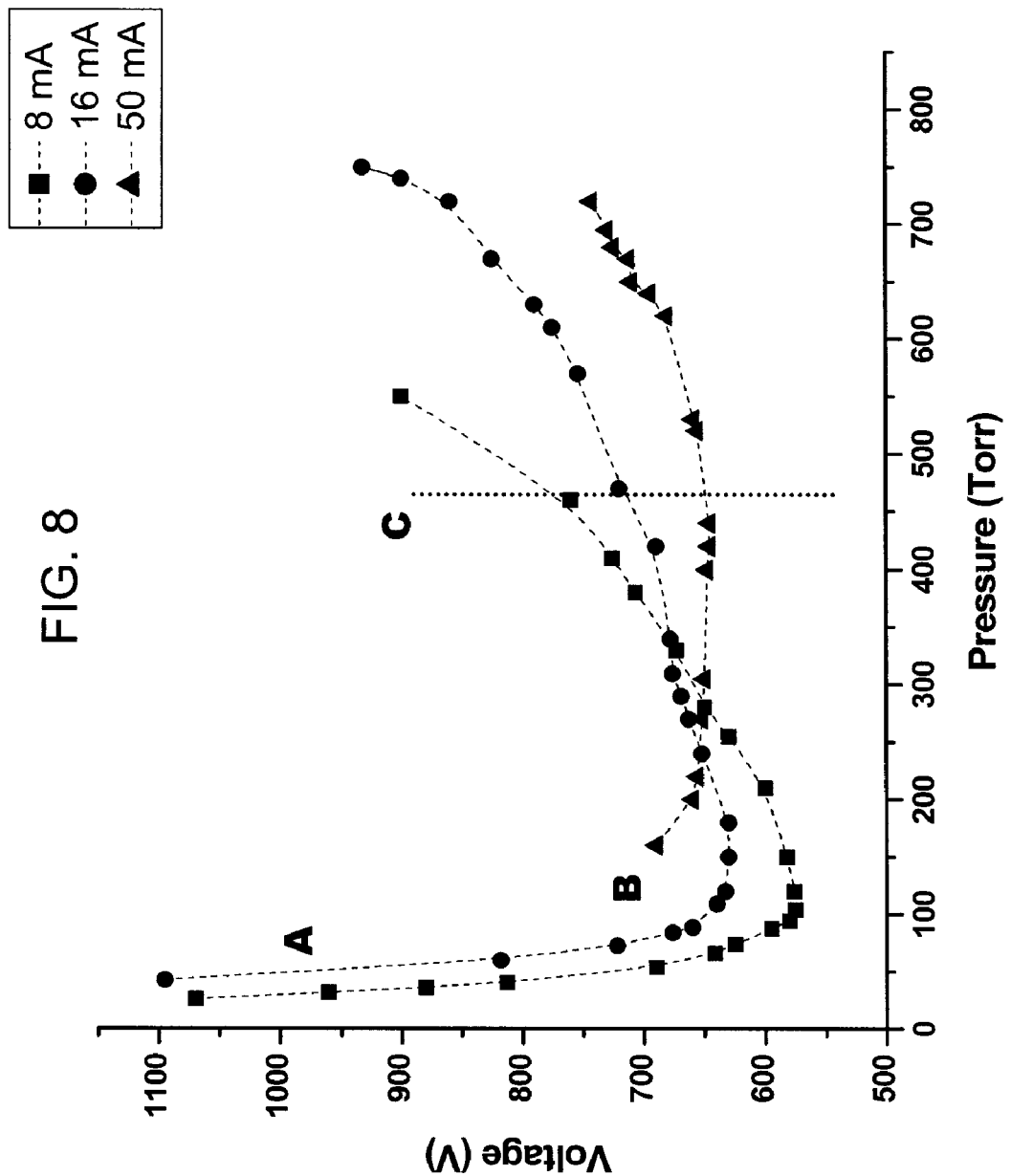
FIG. 8 is a plot of ambient pressure effect on glow discharge voltage at various currents.

The influence of pressure may be seen more clearly in FIG. 8, where the voltage required for sustaining the discharge is plotted as function of pressure while a constant current is maintained. Two well-defined regions can be seen in this plot. At low pressures (<100 Torr), the voltage drops markedly as the pressure is raised. In this pressure regime, electrons require progressively less voltage to produce a given number of ionizing collisions as gas density goes up, because their mean-free path becomes smaller and losses to the walls of the discharge cell are reduced. At pressures around 100 Torr, however, the trend is reversed: a minimum voltage is reached, and the required discharge voltage increases with pressure. This trend at higher pressures can be explained by the necessity of overcoming the greater collisional frequency (i.e., reduction of the electrons' mean free path) by applying higher voltages. In other words, as the pressure is raised the amount of energy that the electrons can gain from a constant field is lessened. Thus, the ionization efficiency drops, and higher voltages are required to sustain the discharge. Region A on the left side FIG. 8 (where voltage drops as the pressure goes up) is coincident with the observed reduction of the volume of the negative glow. Additionally, the inflection point of this plot (see section B in FIG. 8) corresponds to the appearance of emission at the anode end of the positive column.

Figure 7B:
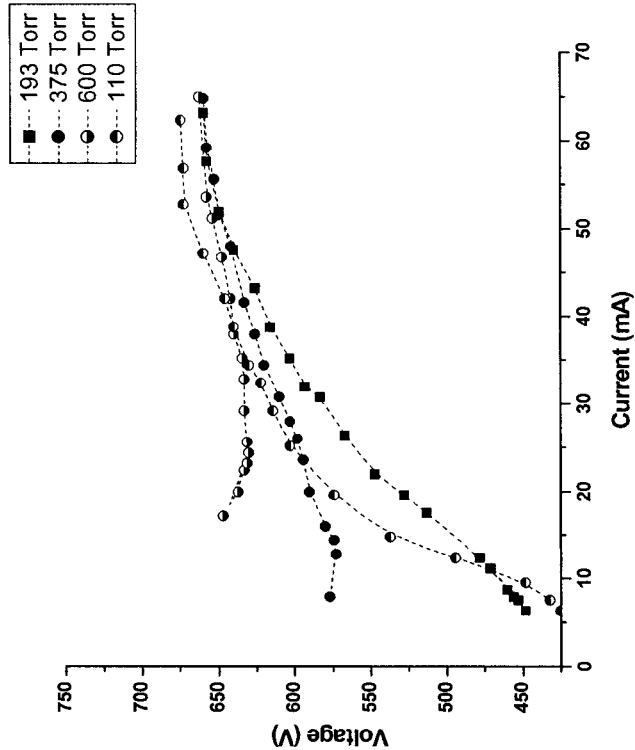
FIG. 7(b) is a plot of current-voltage curves for a glow discharge at various pressures.
Figure 7A:
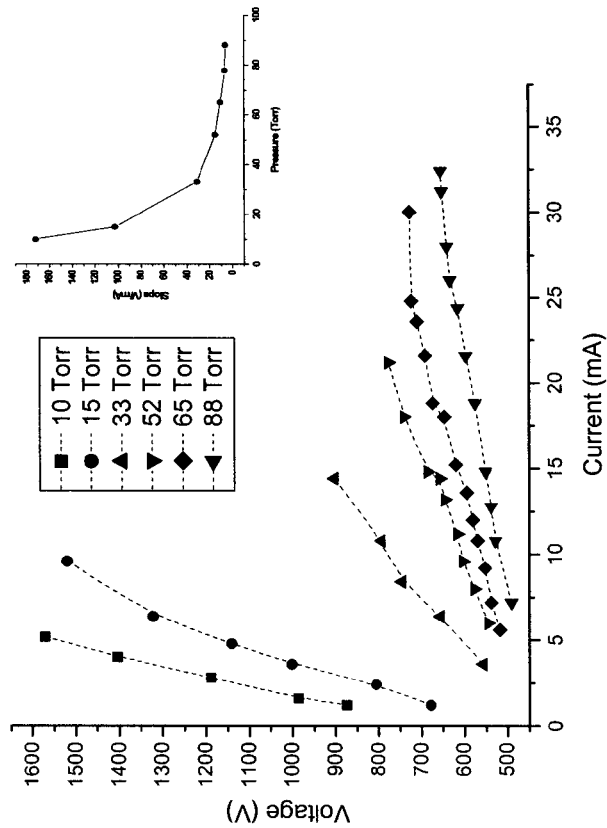
FIG. 7(a) is a plot of current-voltage curves for a glow discharge at various pressures.

The rate of growth of the voltage with pressure in the medium to high pressure range (100-760 Torr) of FIG. 8 is inversely related to the discharge current. For low currents (<20 mA) a marked increase in the voltage as a function of pressure is observed, while for currents above 60 mA the voltage (approximately 650 V) is nearly independent of pressure over a wide range. It has also been found that there is a threshold value (~950 V under the present experimental conditions) above which the discharge becomes unstable and forms an arc. Moreover, the higher the slope of the voltage vs. pressure plots, the lower the pressure at which the system becomes unstable. For this reason, the glow discharge could not be sustained at atmospheric pressure at currents below 20 mA. Accordingly, plots such as those in FIGS. 7(a), 7(b), and 8 are useful to identify stability windows, i.e., conditions where the glow discharges can be sustained in a high-pressure regime. These stability windows are, not surprisingly, strongly dependent on the system geometry, and particularly on the inter-electrode gap between the anode 36 and the cathode 38. The smaller the gap, the broader the stability region becomes. For gaps of 5 mm, the GD cell 26 can be operated at atmospheric pressure with currents as low as 5 mA. Additionally, the ballast resistor 70 plays a significant role in maintaining a stable discharge. The larger the ballast resistor 70, the broader the range of operating conditions (gaps, currents) where the discharge is stable. By doubling the value of the ballast resistor 70, the discharge could be operated stably at 20 mA.

These results illustrate a transition from a conventional low-pressure helium glow discharge to an atmospheric glow discharge without abrupt changes in the electrical properties. Thus, it is clearly demonstrated that the glow discharge at atmospheric pressure is not an isolated phenomenon attributable to specific, unconventional, and difficult-to-reproduce instrumental conditions or geometries. A dc diffuse discharge in helium may be sustained over a broad pressure range, and the helium glow discharge at atmospheric pressure evolves in a continuous fashion from traditional low-pressure glow discharges.

The electrical behavior of a gas discharge is often used as a way of classifying its working regime. For purposes of the present disclosure, when a glow discharge voltage is independent of the operating current, the discharge is considered to be operating in the "normal" mode, whereas if the voltage rises with current, the glow discharge is viewed as operating in "abnormal" mode. In terms of these definitions, glow discharges at atmospheric pressure exhibit unique behavior. Above a certain pressure (see point C in FIG. 8), glow discharges have a negative dynamic resistance, i.e., lower voltages are required to sustain higher currents.

Figure 9B:
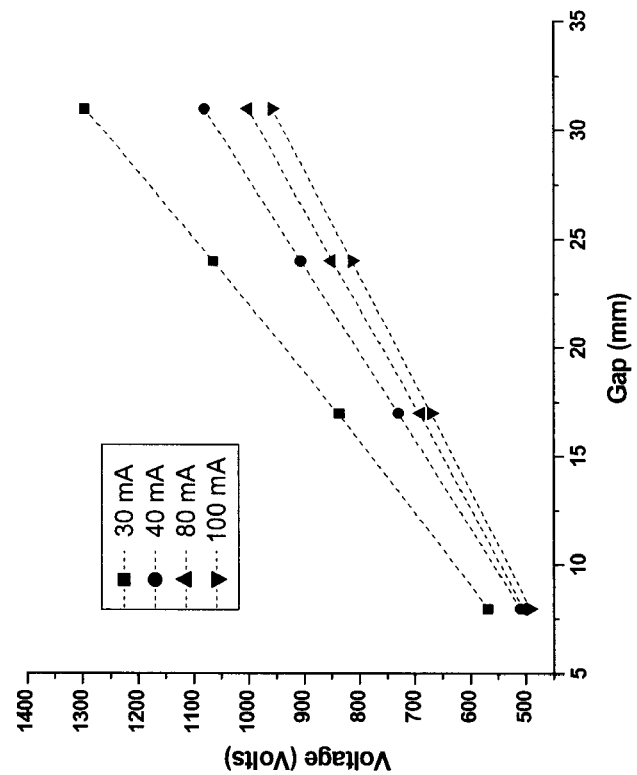
FIG. 9(b) is a plot of voltage-gap distance between electrodes in a helium atmospheric-pressure glow discharge.
Figure 9A:
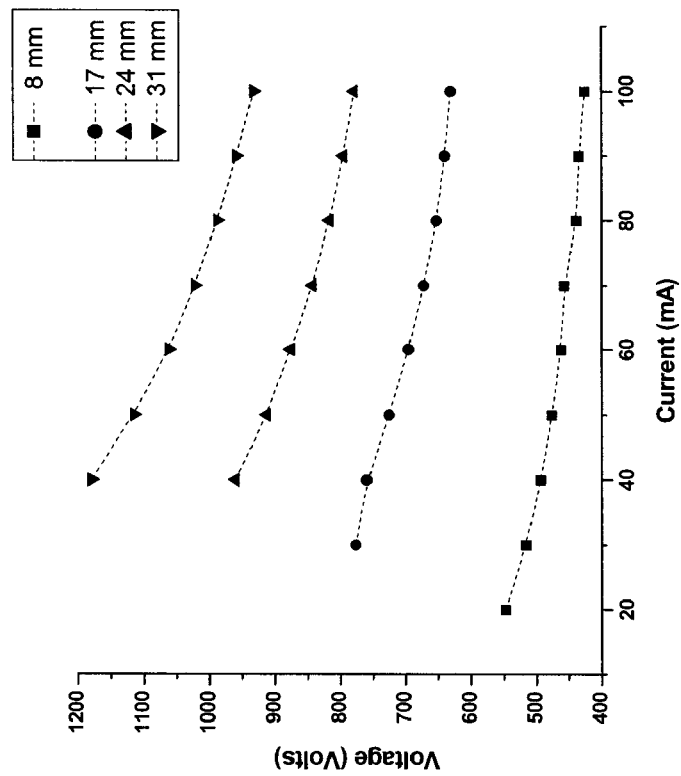
FIG. 9(a) is a plot of current-voltage behavior of a helium atmospheric-pressure glow discharge.

FIG. 9(a) is a plot showing this behavior in more detail for a glow discharge at atmospheric pressure with different inter-electrode gaps. The slopes of these current-voltage curves become more negative as the gap is increased. The negative dynamic resistance of atmospheric pressure glow discharges is well known, and for this reason the ballast resistor 70 is used. The ballast resistor 70 serves to limit the power supplied to the discharge, thereby avoiding arcing. Therefore, a larger ballast resistor 70 (5 kΩ) was used in various embodiments to evaluate larger gaps in FIG. 9(a). In FIG. 9(b), the linear effect of the inter-electrode gap between the anode 36 and the cathode 38 on the discharge voltage is shown explicitly. In the GD cell 26 shown of FIG. 2, gaps between the anode 36 and the cathode 38 up to 4 cm may be employed. However, preliminary exemplary experiments with an alternative cell design permitted generation of a stable discharge with gaps of up to 12 cm, provided a sufficiently large ballast resistor 70 (capable of compensating for the negative dynamic resistance of the atmospheric-pressure glow discharge) was used.

It may also be shown that the atmospheric-pressure glow discharge can actually be considered a glow as opposed to a specialized form of an arc. Given the marked differences between the two regimes, this distinction is relevant from both an analytical and theoretical point of view. The electrical characteristics of the atmospheric-pressure glow discharge strongly suggest that this discharge is, in fact, not operating as an arc. First, arcs function at lower voltages (typically less than 100 V). Second, the transition from a glow discharge to an arc is clearly seen as a marked drop in the operating voltage of the discharge, which has not been observed in the present experiments. Third, arcs typically run with current densities of at least 100 A/cm$^2$, while in the current experiments the maximum cathodic current density was 1.4 A/cm$^2$ (for a 100 mA current). Although it is true that the anodic current density is considerably higher, this discharge did not become filamentary in the illustrative experiments, even when large gaps were tested. Such behavior was maintained even at the highest currents (100 mA) investigated here. This "glow" regime may, in fact, be sustained for currents up to several amperes.

Although the information described previously is relevant for the operation of an atmospheric pressure glow discharge, the ultimate goal of an analytical plasma source is to produce an efficient transfer of energy from the electrical field to the electrons and the buffer gas, which can then be utilized for the desorption, ionization, and excitation of analyte species. For this reason, spectroscopic characterization may assist in determining the applicability of the plasma as an analytical source.

For the illustrative spectroscopic experiments performed, the vacuum 29 was disabled and the GD cell 26 was positioned in the ACTIVA ICP compartment. The anode 36 and cathode 38 were aligned with the ICP torch axis, so the entire gap between anode 36 and 38 was focused onto the entrance slit of the spectrometer. First, UV-Visible spectra were collected over the range 160-800 nm with no spatial discrimination at different integration times in order to verify the absence of self-absorption effects. Then, emission maps of selected spectral regions were generated.

Figure 10:
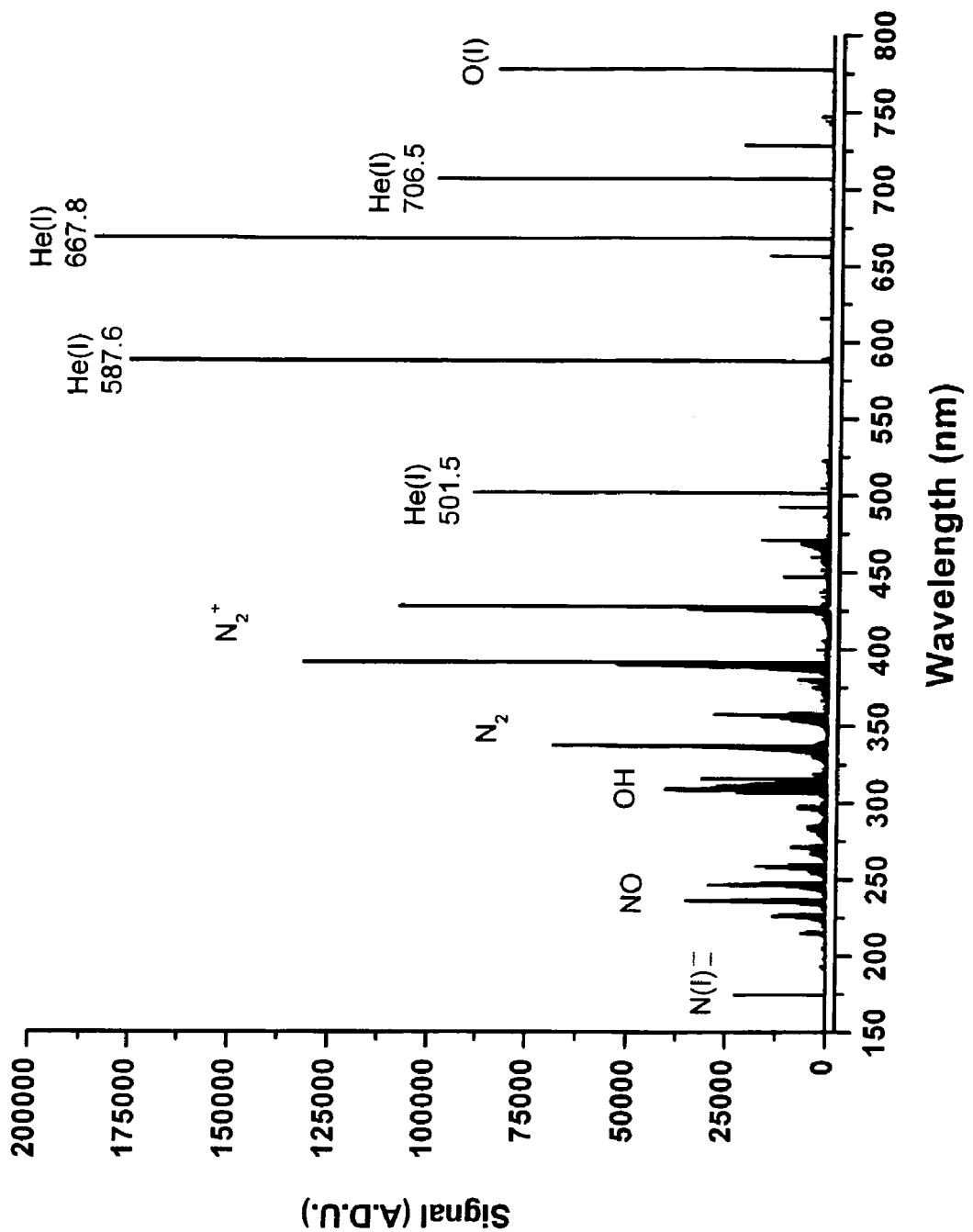
FIG. 10 shows a UV-Vis emission spectrum of a helium atmospheric-pressure glow discharge.

FIG. 10 shows an UV-Visible spectrum of the GD cell 26 used in this study. Apart from the helium lines, emission from several impurities (trace amounts of $N_2$, $H_2O$, $O_2$) can be observed. In spite of the high-purity helium used and several attempts to purify the gas on line (drying, traps, etc.), emission from these species was typically present. Difficulties associated with the purity of the gas in helium-based discharges are well known, because the high ionization/excitation efficiency of these plasmas allows impurities to be detected at very low levels. Removing these impurities often requires extensive cleaning and baking of the gas lines and special purification strategies (such as cataphoretic purifiers). However, these measures were not considered necessary for the present disclosure.

Apart from the He(I) lines, the most intense emission from the discharge is attributable to $N_2^+$ (band heads at 391.4 nm and 427 nm). Characteristic emission from N(I) (lines at 1.74.3 and 1.74.5 nm), $N_2$ (band heads at 337 and 380 nm), OH (band heads at 281 and 306 nm), NO (γ system with double-headed bands below 300 nm) and O(I) (triplet at 777.2, 777.4 and 777.5 nm) is also observed. The ability to detect these impurities, particularly in the positive column, was improved by the extremely low background levels observed in the emission spectrum. Importantly, emission from the cathode material (W) was not detected, probably because of the low sputtering efficiency of helium.

The spatial distribution of selected emission features of the illustrative experiments described is shown in FIGS. 11(a)-12(b) (solid line 30 mA, dashed line 50 mA). The arrows in each figure indicates the position of the cathode. All the helium lines that were studied (501.5 nm, 587.6 nm, 667.8 nm and 706.5 nm) have a similar pattern (FIG. 11(a)): the emission is very intense in regions close to the electrodes, and it is stronger at the cathode than at the anode. It is also found that the increase of emission with current is more pronounced at the anode than at the cathode. Emission from the nitrogen molecular ion ($N_2^+$) (see FIG. 11(a)) has a pattern similar to that of helium lines (see FIG. 11(b)). This similarity might be related to the mechanism of production of this ion. There is widespread agreement that $N_2^+$ is formed in helium discharges through both Penning ionization and charge transfer, both of which involve helium:

$$He^* + N_2 \rightarrow He + N_2^+ + e \quad (1)$$

$$He_2^+ + N_2 \rightarrow 2He + N_2^+ \quad (2)$$

Figure 11B:
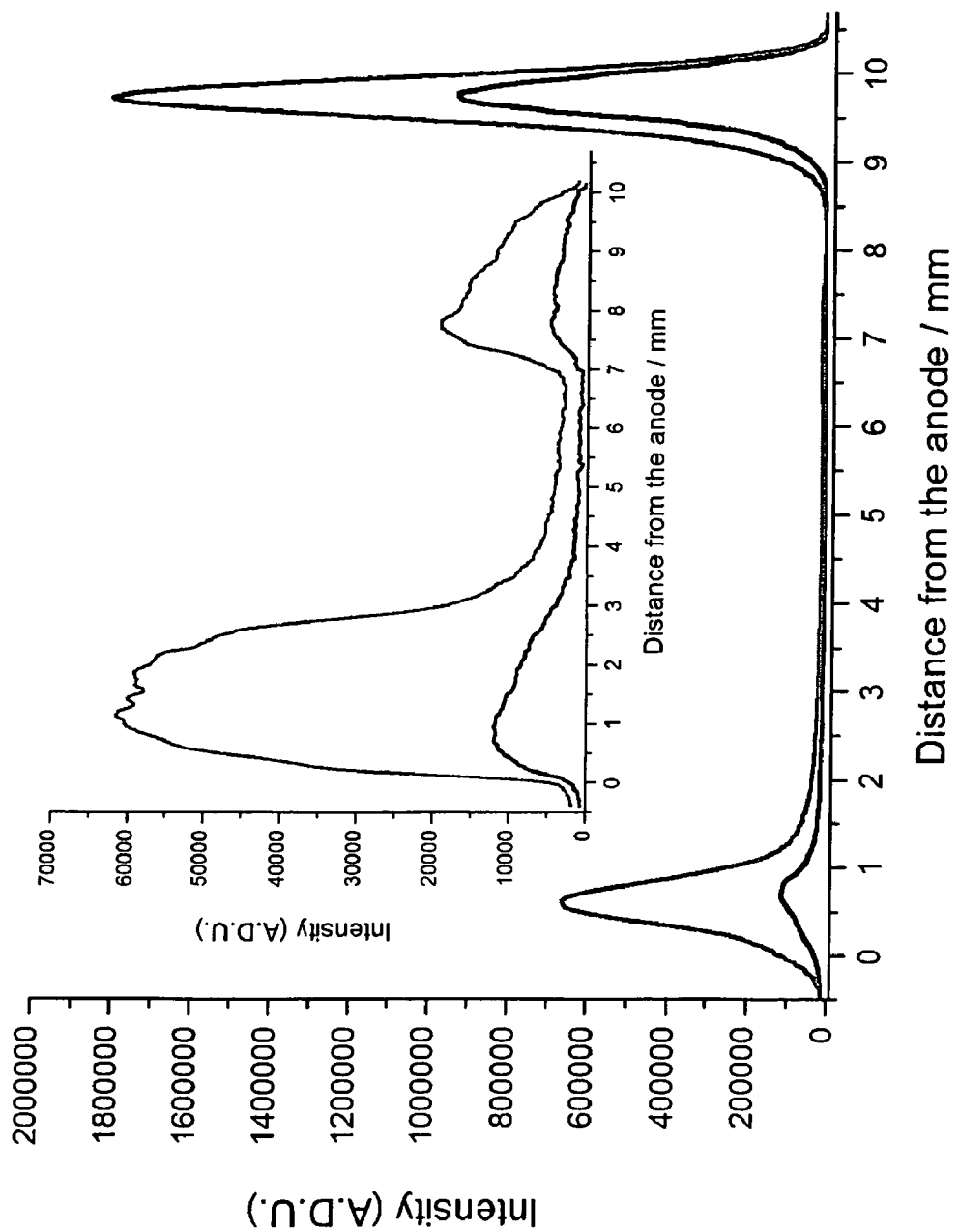
FIG. 11(b) shows spatially resolved emission from $N_2^+$ in a helium atmospheric pressure glow discharge at two different discharge currents and an inset plot showing the spatially resolved emission from atomic nitrogen in a helium atmospheric pressure glow discharge at two different discharge currents.

The $N_2^+$ ion is initially formed in an excited state and upon decay, the characteristic emission of the first negative system (band head at 391.4 nm) can be seen. For this reason, the emission of $N_2^+$ has been used as a way of detecting the presence of both $He_2^+$ and $He^*$. Although it is not possible to determine a priori which of these reactions (1 or 2) will be dominant, it is evident that some species in the regions close to the electrodes have enough energy to efficiently ionize and excite $N_2$, whose ionization potential is 15.6 eV. In FIG. 11(b), (see inset plot) the spatial distribution of atomic nitrogen is shown. It has been previously found that $N_2^+$ can be quickly destroyed by dissociative recombination:

$$N_2^+ + e^- \rightarrow N + N^* \quad (3)$$

(where N* is a nitrogen atom in an excited state); because of the high rate constant of this reaction, this might be—at least in part—the source of atomic nitrogen.

Figure 12A:
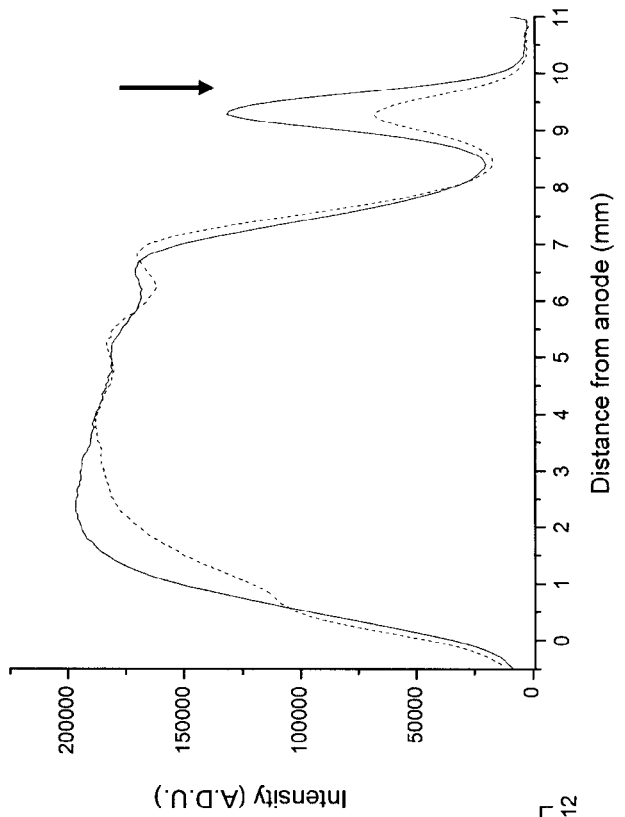
FIG. 12(a) shows spatially resolved emission from $N_2$ in a helium atmospheric-pressure glow discharge at two different discharge currents.
Figure 12B:
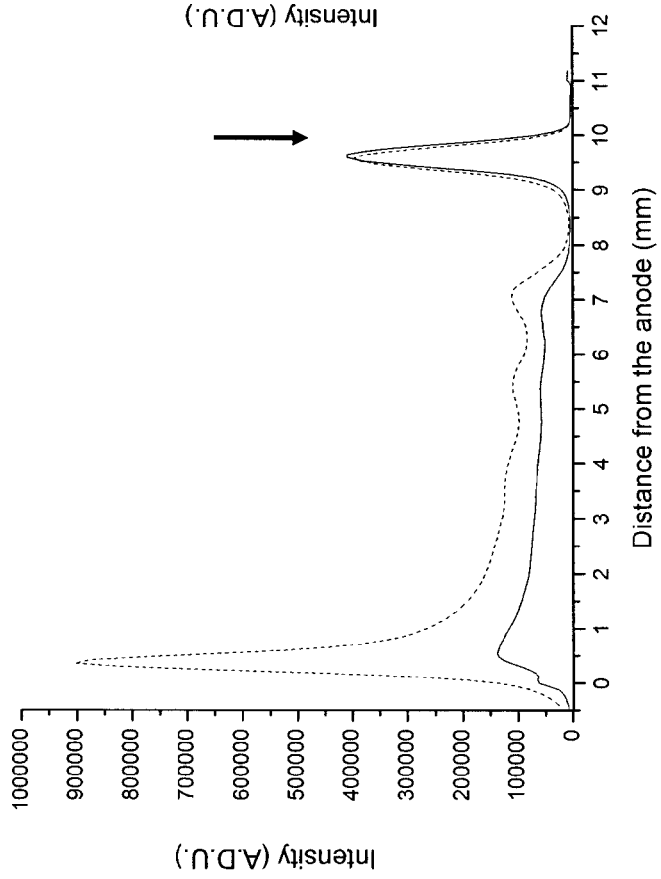
FIG. 12(b) shows spatially resolved emission from NO in a helium atmospheric-pressure glow discharge at two different discharge currents.

Unlike the profiles in FIGS. 11(a)-(b), the emission from some molecular species ($N_2$, NO) is particularly intense in the positive column (see FIGS. 12(a) and 12(b)). For $N_2$, the emission close to the anode 36 and cathode 38 is always higher than in the positive column. The emission in the anode region becomes considerably stronger than that in the negative glow as the current is raised (see FIG. 12(a)). The emission from NO, on the other hand, is always higher in the positive column and, unlike any other profile, the emission in the negative glow drops as current is increased (see FIG. 10(b)). It is believed that this drop may be due to dissociation of NO at higher currents.

Emission maps of OH are shown in FIG. 13(a) (solid line 30 mA, dashed line 50 mA). These profiles are similar to those found for nitrogen in FIG. 12(a), with significant emission in the positive column and particularly strong emission in the vicinity of the anode 36 and cathode 38. Also, as the current grows, the OH emission near the anode 36 becomes prominent. From these emission maps, rotational-temperature profiles were calculated (FIG. 13(b)). Rotational temperature profiles were estimated from emission maps of the Q1-branch of the OH emission. Triplicate spectra were used. In one embodiment, Boltzmann plots were linearized and the slope was calculated by the least-squares fit method. Temperature values with more than 20% RSD or generated from regression lines with a correlation coefficient lower than 0.85 were eliminated. The temperature in the region close to the cathode 38 could not be estimated within acceptable limits of tolerance for the error. This large error might be a result of the high temperature gradient in this region and the limited spatial resolution (in the fractional mm range). Temperatures in the positive column range from approximately 1300 K at 30 mA to 1500 to 1800 K at 50 mA. These values are considerably higher than are commonly found in corona discharges, making the glow discharge useful for the desorption or ionization of less volatile or more refractory compounds. Temperatures tend to rise towards the anode 36, a trend that is more pronounced at higher currents.

Another aspect of the maps of FIGS. 11(a)-13(b) is the clear evidence of a well-defined spatial structure in the discharge, which reflects the precise gradients of electrical potential that are generated between the electrodes. This precise distribution of electrical fields is, in fact, a distinctive feature of glow discharge cells. Unlike other gas discharges, glow discharges can "hold" large electrical potentials between the anode 36 and the cathode 38 due to the generation of a space-charge structure in the vicinity of the cathode 38. Thus, electrons may gain a large amount of energy in the region close to the cathode, but they are slowed down as they move farther away from it. This structure prevents an ionizing cascade that would lead to an arc. Because of this process, electrical energy can be transmitted to a buffer gas from the electrons in a non-thermal fashion in particular regions of the discharge. The dark space separating the two strongly emitting regions (i.e. the negative glow and positive column) is evidence of the non-thermal nature of this source. Such spectroscopic evidence adds support to the idea that the discharge in a glow discharge cell is effectively a glow. As a distinct feature of glow discharge cell sources, however, emission from the anode 36 end of the positive column is qualitatively similar to the emission in the cathodic region adjacent the cathode 38.

Thus, it is possible to sustain a discharge with a glow-like structure at atmospheric pressure. Based upon the results described herein it is believed that at higher pressures diffusional losses (losses to the walls and the electrodes) become less important, while recombination should be the dominant mechanism for charge loss. It has been shown that that $He_2^+$ becomes a dominant species as the pressure is increased in a glow discharge, and it has also been estimated that the same ion should be the main source of helium metastables in the afterglow of a He discharge at atmospheric pressure. Due to the nature and structure of the atmospheric pressure glow discharge, the positive column should have a substantial influence on the overall behavior of the discharge. Several studies have shown that, under certain operating conditions, the positive columns of low- and medium-pressure glow discharges show a negative dynamic resistance. This effect is particularly present at low currents, and has a significant impact on the properties of the entire glow discharge.

Previous glow discharge configurations in the flowing afterglow (FA) mode have shown promise for the ionization of various compounds including organic ones. In this configuration, reactive species generated in the glow discharge (ions, metastables, etc) are used downstream to ionize target molecules. The fast flowing afterglow (FFA) and the proton-transfer reactor (PTR) are examples of this strategy. In the FFA, argon is used as a support gas and reaction with argon metastables leads to the ionization of the target molecules. In the PTR, a glow discharge sustained in a helium-water-vapor mixture generates ionized water clusters, which are used to ionize analytes that have a high proton affinity. Both strategies operate at low pressure.

In the embodiment of FIG. 3, an atmospheric-pressure glow discharge ignited between the pin-cathode 52 and the anodic plate 56 was initially operated at 20 mA. Helium was provided to the GD cell 50 at 0.8 l/min. As is common in atmospheric-pressure chemical ionization (APCI) mass spectrometry sources, a slight positive potential (~30 V) was applied to the sampling plate 94. The MS operating potentials were similar to those used with the ICP source. Results showed that the ion signal was influenced by biasing the GD cell 50 at a slightly positive potential. As a result, in the embodiment shown in FIG. 3, the anode 56 was connected to the individual low-voltage power supply 72 and floated at approximately +30 V.

Under these conditions, intense background-ion signals for ionized water clusters ($[H_2O]_nH_3O^+$, with n from 1 to 6), $NO^+$ (m/z=30), $O_2^+$ (m/z=32) and, to a lower degree, $H_2O^+$ (m/z=18) and $N_2^+$ (m/z=28) were detected. Many of these species are the result of the ionization of atmospheric components. The generation of ionized water clusters is usually considered the product of the reaction of $N_2^+$ with water molecules (moisture present in the atmosphere). These reactions are relevant because water clusters are the main reagent ions in atmospheric-pressure chemical ionization sources.

In another illustrative experiment, the GD cell 50 of FIG. 3 was mounted on an x,y,z translation stage and aligned with the sampling orifice of the interface 90 of a mass spectrometer 88. The EDC 78 temperature was adjusted to approximately 200° C. unless stated otherwise herein. Operating conditions (current and gas flow) were adjusted to obtain maximum ion signal. Qualitative mass spectra were obtained after approximately 2 minutes of injecting a given amount of a compound (~50 μg) into the EDC 78. For evaluation of the quantitative aspects of the GD cell 50 operated at atmospheric pressure time-resolved profiles of the whole transient at selected m/z values were obtained.

Figures 14A, 14B:
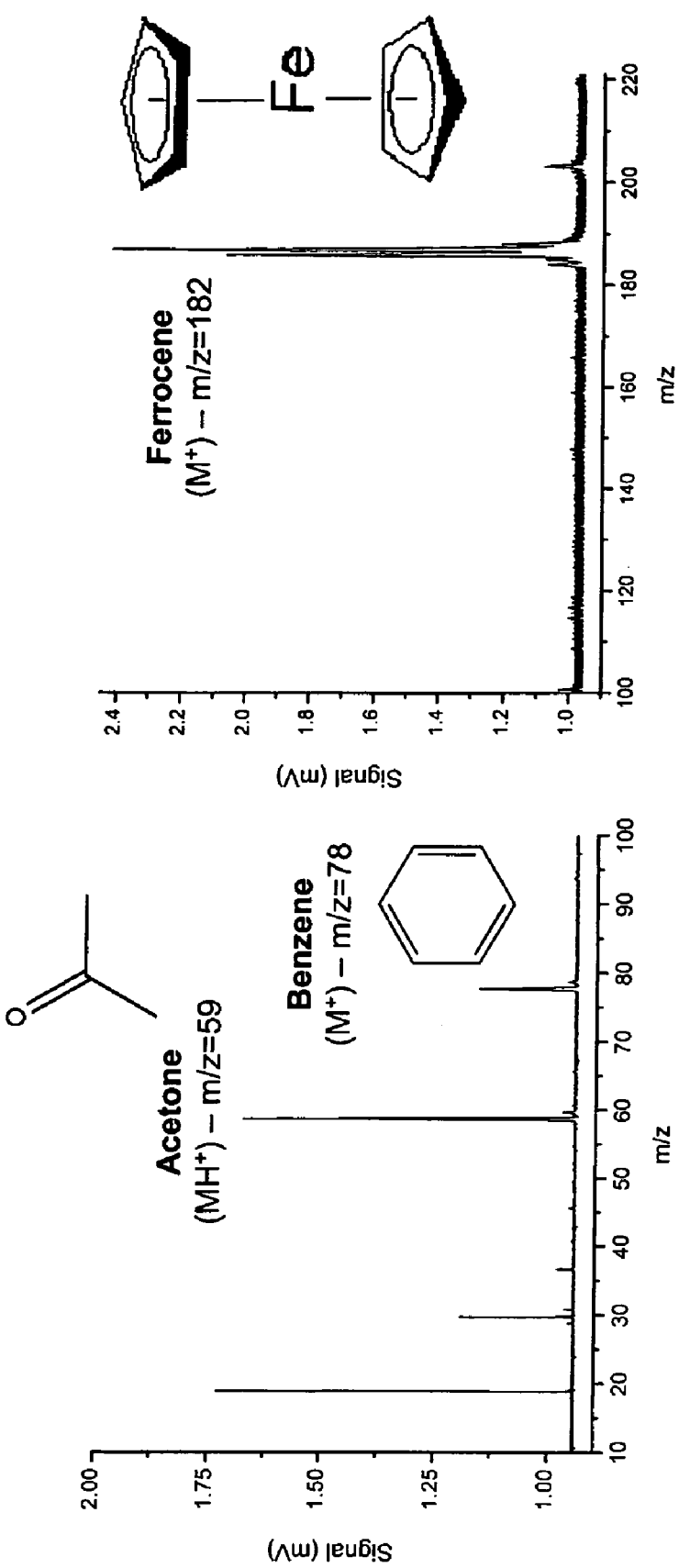

The operating conditions of the atmospheric-pressure glow discharge were adjusted to maximize these background-ion signals. Optimal conditions in one embodiment are compiled in FIG. 18. The optimal values for operation of the time-of-flight mass spectrometer 88 were not significantly different from those used with the ICP source. Following this optimization, a wide range of organic compounds (acetone, benzene, aniline, and others) were successively injected into the ESD 78. Strong signals at the m/z value corresponding to the molecular ion ($M^+$) or the protonated molecular ion ($MH^+$) (m/z=59) for acetone were observed. Re-optimization of the operating conditions to maximize this $M^+/MH^+$ signal yielded results similar to those in FIG. 14 and FIG. 15.

In general, polar compounds (alcohols, ketones, ethers, amines, acids, etc.) yield the $MH^+$ ion as the main (and in most cases the only) peak. Less polar substances (benzenes and their derivates, halogenated hydrocarbons, etc.) yield mostly the $M^+$ peak. Selected spectra of compounds that were tested are presented in FIG. 14(a)-(d) and FIG. 15(a)-(d). The plots shown in FIG. 14(a)-(d) are for vapor-phase samples. The plots shown in FIG. 15(a)-(d) are results from solid samples. The shaded areas cover background peaks. All the volatile organic compounds that were tested yielded the $M^+/MH^+$ or some large fragment ion signal. FIG. 19 summarizes some of the compounds that were examined and the main ion peaks that were observed.

Figure 15A:
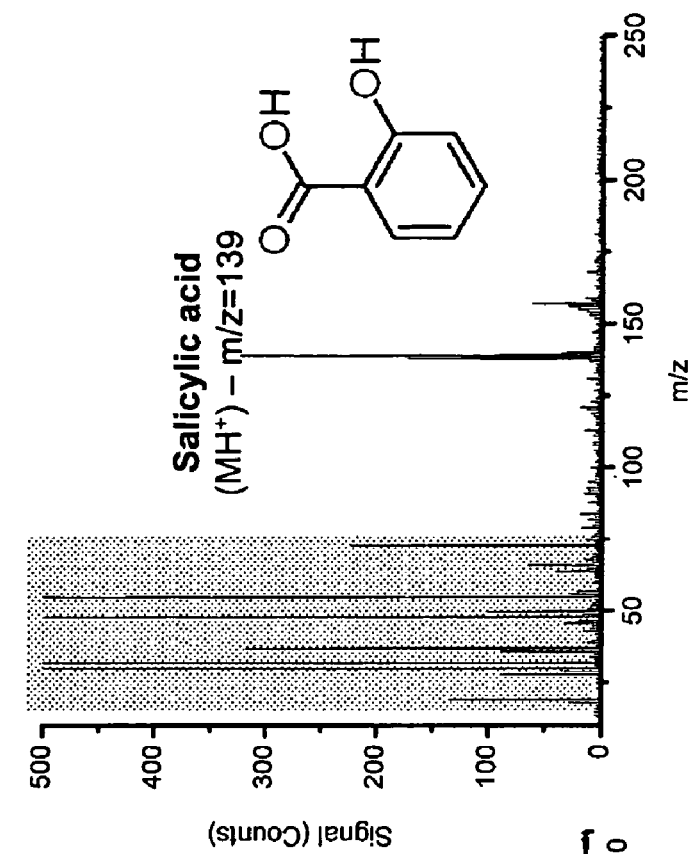
FIGS. 15(a)-(d) shows mass spectra of various solid compounds.
Figure 15B:
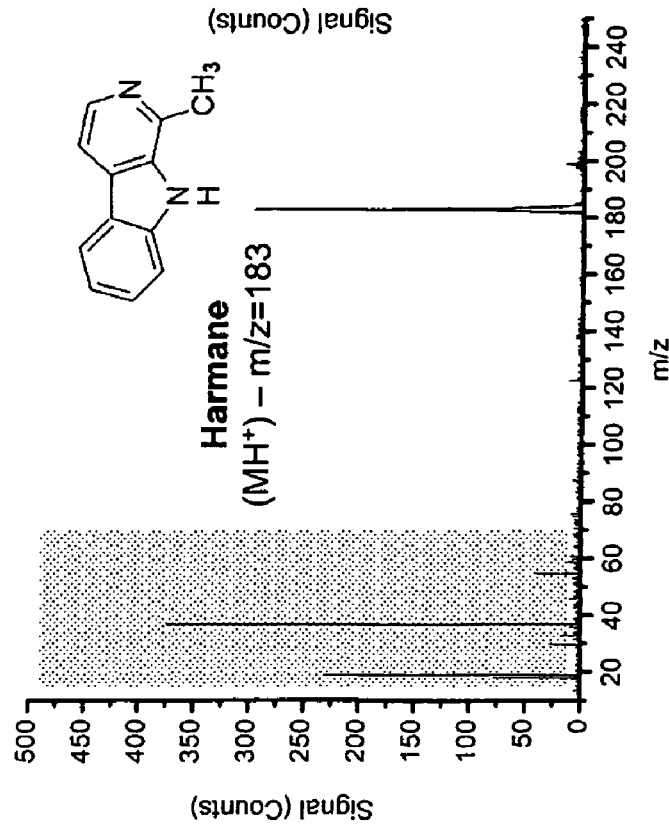
Figure 15D:
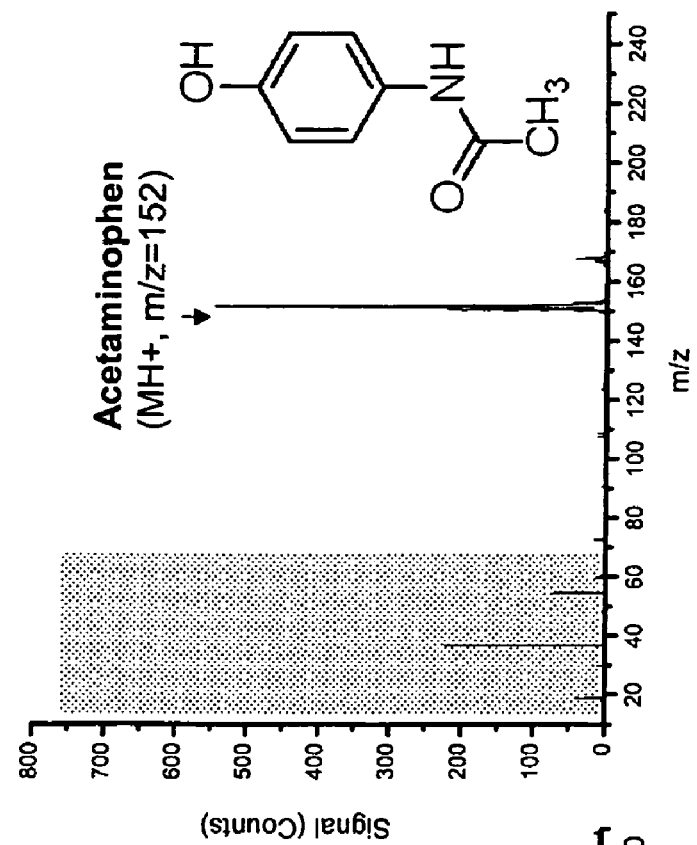
Figure 15C:
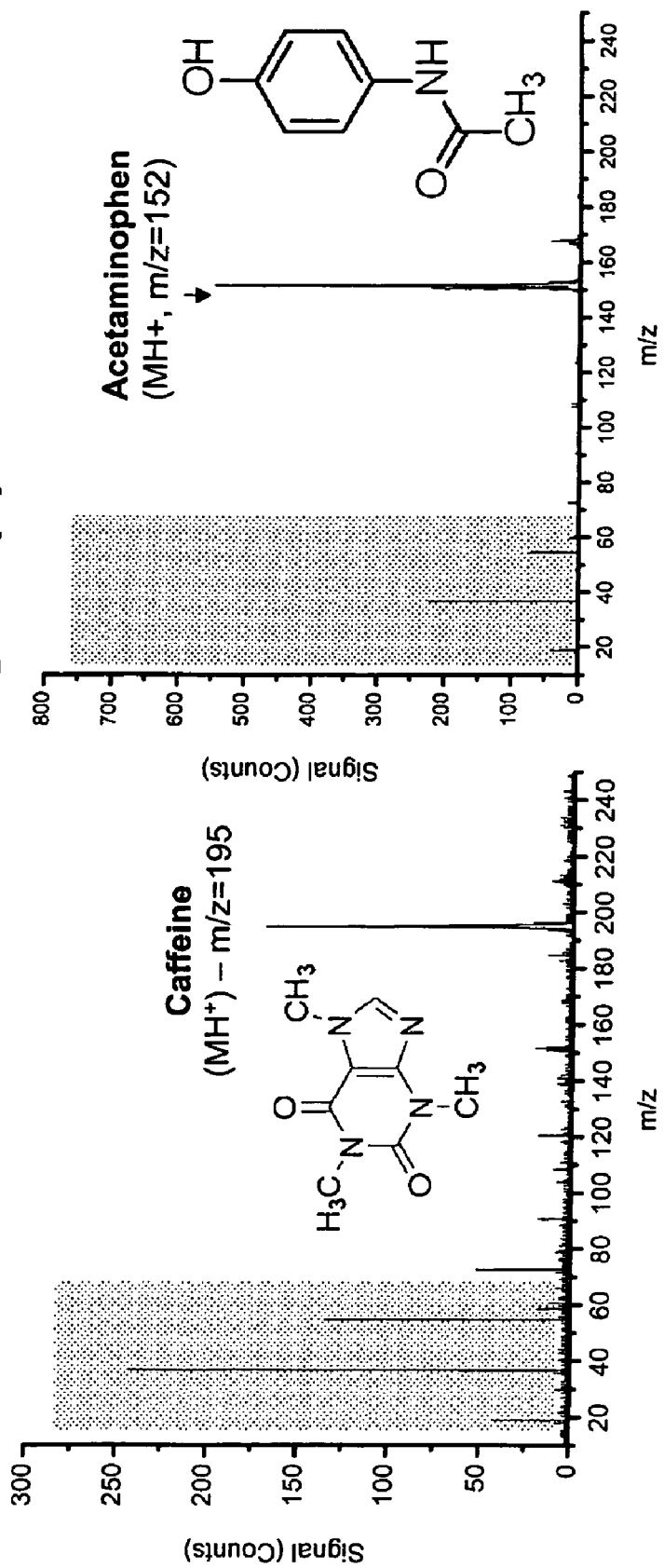

In one embodiment, pharmaceutical tablets may be analyzed directly by exposing them to the flowing afterglow of an atmospheric-pressure glow discharge using helium as a carrier gas. For example, the mass spectrum of a Tylenol® tablet exposed to the flowing afterglow for 2 seconds reveals the main component, acetaminophen, as one of the most prominent peaks in the spectrum, as shown in FIG. 15(d). In other illustrative experiments, pharmaceuticals such as ibuprofen, naproxen, flurbiprofen, diclofenac, and foodstuff (i.e., vanilla extract, mint, tea leaves) have also been inserted into the flowing afterglow, yielding ions of their characteristic chemical components. An example is shown in FIG. 15(c), where an intact coffee bean was exposed to the afterglow, yielding a peak typical for caffeine ($MH^+$ at m/z 195). In one embodiment, detection of caffeine in beverages was performed by drying a sub-microliter volume on a filter paper that was then introduced into the afterglow.

Figure 17:
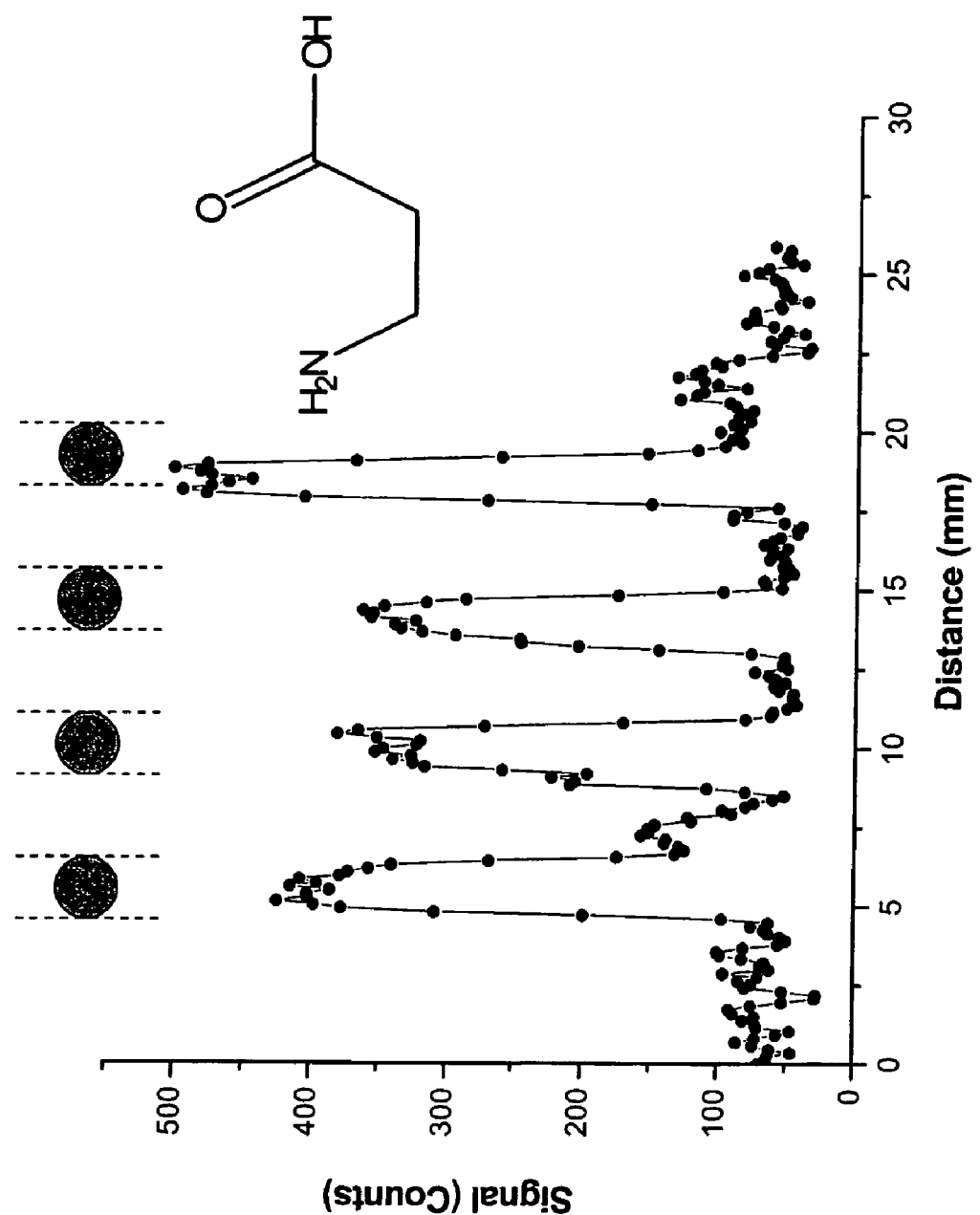
FIG. 17 shows a plot demonstrating spatial resolution of a flowing afterglow-based analysis.

Another illustrative application of the GD cell 50 is the generation of spatially resolved MS profiles. In one embodiment, the orifice 66 in the anode 56 of 0.8 mm, the stream of excited species leaves the GD cell 50 discharge at relatively high speed (calculated to be approximately 10 m/s). This stream of effluents can then be rastered across a target surface of a sample in order to locate or map organic substances. In one embodiment, a demonstration of spatially resolved analysis was performed using a series of 1-μl droplets of a $10^{-3}$ M β-alanine solution dried on a strip of filter paper. A rotating autosampler allowed the paper to be scanned in front of the afterglow being emitted from the GD cell 50. The results, as shown in FIG. 17, demonstrate that it is possible to map ion signals with single-mm spatial resolution. Moreover, this resolution was limited here by the step size in the stepper motor, a problem that will be overcome in future experiments. It should be appreciated that alternatives such as the incorporation of a nozzle at the anode orifice, and the use of a capillary sampling interface in the mass spectrometer 88 are considered and may improve spatial resolution. The peaks shown in FIG. 17 correspond to sub-nanogram amounts. Therefore, the system could be applied, for example, to the scanning of thin layer chromatography plates.

It should be appreciated that various types of samples may be analyzed through application of a GD cell. As with other approaches for ambient mass spectrometry, the desorption-ionization can be performed on a wide variety of substrates: paper, synthetic membranes (e.g., Teflon®, polyethylene, polymethylmethacrylate) wood, cloth, glass, and solid samples themselves. Usually, nonpolar substrates yield better sensitivity.

These results show that the atmospheric-pressure glow discharge cell using a carrier gas, such as He, can be used as a qualitative tool for the ionization of a wide variety of organic compounds. For the polar compounds, proton transfer appears to be the dominant ionization mechanism. In this way, the flowing afterglow emitted from a GD cell behaves similarly to an APCI source, but with enhanced ionization capabilities. For non-polar compounds, it is believed that the ionization may occur through charge transfer (from $NO^+$, $N_2^+$, etc.) or Penning ionization (through $He^*$). Regardless, the ionization is extremely "soft", i.e., it does not yield significant fragmentation, which leads to a relatively simple mass spectrum (see FIGS. 14(a)-(d) and FIGS. 15(a)-(d)). In some cases, because of the nature of the target molecule (especially for large molecules with labile bonds) fragmentation cannot be avoided. Where fragmentation does occur, however, it is typically very reproducible and simple to interpret.

In addition to this attractive performance as a qualitative tool, quantitative aspects should be considered. First, the spectra in FIG. 14(a) correspond to a mass flow in the pg/s range. This value can be estimated from the amount of sample injected, the time constant of the exponential-dilution cell, and the time at which the spectrum was taken after the injection. In particular:

$$C = C_0 \exp\left(-\frac{F}{V} \times t\right) \qquad (4)$$

where C is the concentration at time t, $C_0$ is the initial analyte concentration and V is the volume of the chamber. From this equation, calibration plots can be generated and quantitative features can be evaluated. Although it is not within the scope of the present disclosure to describe exhaustively the analytical features of this source, it should be appreciated that that mass flows in the sub-pg/s range can be readily detected for a wide variety of compounds. This performance leads to detection limits in the single to sub-femtomole range. With the exponential-dilution cell, linear ranges up to 4 orders of magnitude were found.

Figure 16B:
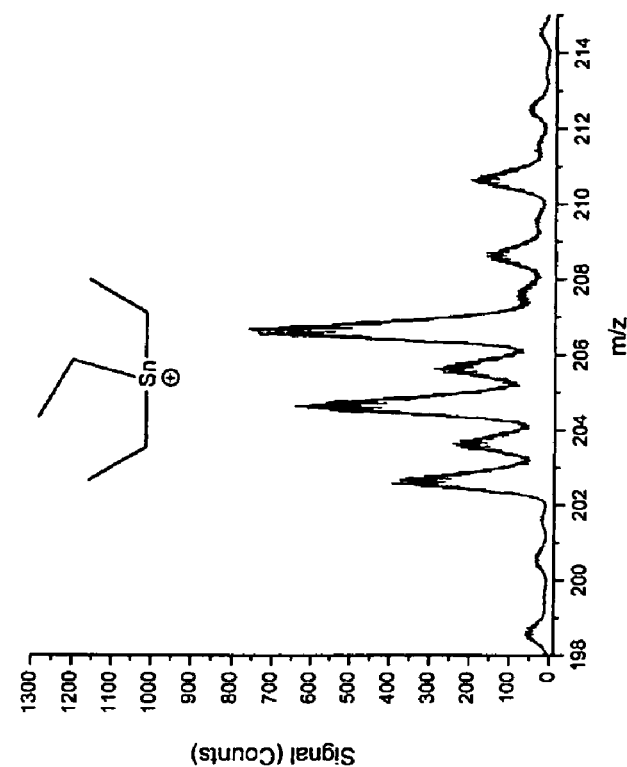
FIG. 16(b) shows main peaks in the mass spectrum of tetraethyltin.
Figure 16A:
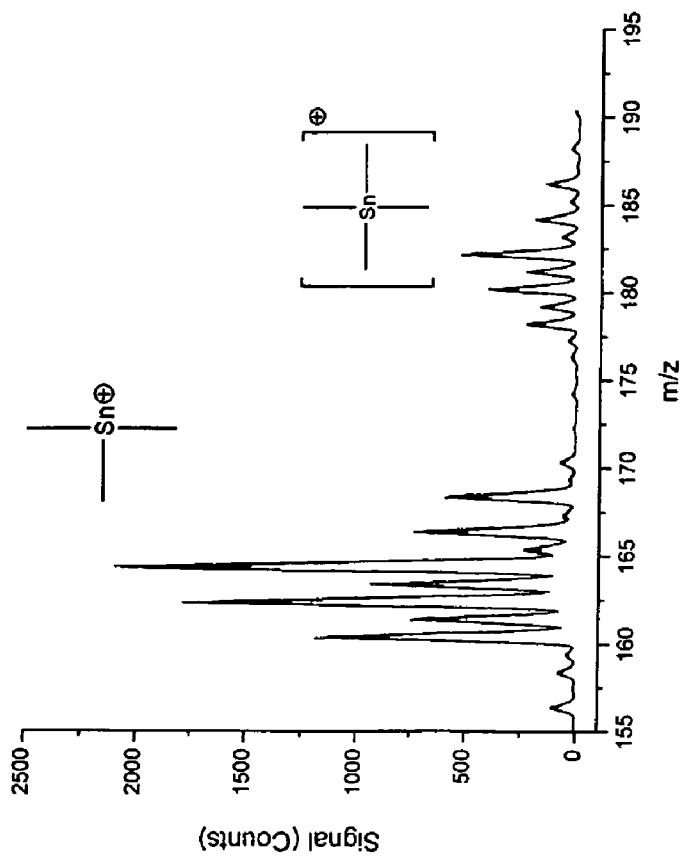
FIG. 16(a) shows main peaks in the mass spectrum of tetramethyltin.

In one embodiment, the GD cell 50 and time-of-flight mass spectrometer 88 may be used for speciation analysis as indicated by the results shown in FIGS. 16(*a*)-(*b*), where the mass spectra of tetramethyltin (TMT, Mr=178.83) and tetraethyltin (TET, Mr=234.94) are presented. For TMT, $M^+$ is not very intense, and the main peak is at m/z~165, which corresponds to the loss of one methyl group ($[CH_3]_3Sn^+$). For TET the molecular ion cannot be seen, and the main peak is at m/z~205, which correspond to the loss of one ethyl group from the molecule ($[CH_3CH_2]_3Sn^+$). In FIGS. 16(*a*)-(*b*), the isotopic pattern of Sn can be clearly seen. Mass flows in the sub-ng/s range could be easily detected.

An additional consideration of an atmospheric-pressure glow discharge lies in the possibility of a miniaturized device. In one embodiment, a preliminary miniaturized version of the flowing afterglow of an atmospheric-pressure glow discharge cell was fabricated with a gap between an anode and cathode of 1 mm, and a discharge chamber with a total volume of 100 µL (limited mostly by the materials used to fabricate the chamber). The discharge (still in the glow regime) was sustained at 250 V and a current between 5-10 mA, thus requiring power in the single watt range. A helium flow was 250 mL/min, although it could be further reduced by reduction of the discharge chamber volume. When used with the present time-of-flight mass spectrometer, similar reagent ions, signal levels, and overall performance were obtained as with larger-scale atmospheric-pressure glow discharge cells described herein.

There are a plurality of advantages of the present disclosure arising from the various features of the apparatus and methods described herein. It will be noted that alternative embodiments of the apparatus and methods of the present disclosure may not include all of the features described yet still benefit from at least some of the advantages of such features. Those of ordinary skill in the art may readily devise their own implementations of an apparatus and method that incorporate one or more of the features of the present disclosure and fall within the spirit and scope of the present disclosure.

The invention claimed is:

1. A method for ionizing and desorbing a sample for analysis, the method comprising the steps of:
    establishing an inter-electrode gap between a first and second electrode of between 1 mm and 120 mm,
    energizing the first and second electrode to produce a glow discharge at atmospheric pressure with a current in excess of about 5 mA, wherein the glow discharge has a negative dynamic resistance,
    supplying a carrier gas to at least a portion of the glow discharge to create effluents thereof, and
    conducting the effluents of the glow discharge to the sample to desorb and ionize the sample for analysis.

2. The method of claim 1, wherein the chamber is non-conductive.

3. The method of claim 2, wherein the chamber is formed of Teflon®.

4. The method of claim 1, wherein the supplying a carrier gas to at least a portion of the glow to create effluents thereof comprises supplying helium to at least a portion of the glow to create effluents thereof.

5. The method of claim 4, wherein the supplying a carrier gas to at least a portion of the glow to create effluents thereof comprises supplying helium to at least a portion of the glow to create ions, electrons, and excited species of helium and of residual gases.

6. The method of claim 5, wherein the conducting the effluents of the glow discharge to the sample to desorb and ionize the sample for analysis comprises conducting the ions, electrons, and excited species to the sample to desorb and ionize the sample for analysis.

7. The method of claim 6, wherein conducting the effluents of the glow discharge to the sample comprises rastering the effluents across the sample to desorb and ionize the sample.

8. The method of claim 7, wherein the rastering the effluents of the glow discharge across the sample comprises rastering the effluents across the sample to map species from sample.

9. An apparatus for desorbing and ionizing a sample for analysis comprising;
    a chamber;
    a first electrode and a second electrode spaced apart by at least 1 mm from the first electrode, wherein, at least a portion of each of the first and second electrodes are positioned in the chamber;
    at least one power supply configured to energize the first and second electrode to provide at least about 5 mA of current between the first and second electrodes;
    a ballast resistor configured to limit current supplied to the glow discharge, the ballast resistor having a resistance sufficiently high to avoid arcing between the first and second electrodes,
    a glow discharge having a negative dynamic resistance positioned within the chamber; and
    a gas inlet in the chamber to receive carrier gas from a supply of carrier gas configured to introduce carrier gas to the glow discharge to create effluents of the carrier gas to desorb and ionize the sample for analysis.

10. The apparatus of claim 9, wherein the supply of carrier gas is a supply of helium.

11. The apparatus of claim 10, wherein the a supply of helium is configured to introduce helium to the glow discharge to create ions, electrons, and excited species of the helium, and
    wherein, the ions, electrons, and excited species are introduced to the sample to desorb and ionize the sample for analysis.

12. The apparatus of claim 9, wherein the sample is selected from the group consisting of a gas, a liquid, and a solid.

13. The apparatus of claim 9, wherein the sample is selected from the group consisting of a dry aerosol and a wet aerosol.

14. The apparatus of claim 9, wherein the sample is selected from the group consisting of a mixture and an emulsion.

15. The method of claim 1, wherein the effluents are conducted to the sample through a capillary tube, the tube serving as the counter-electrode.

16. The method of claim 1, wherein the effluents are conducted to the sample through a conductive capillary tube.

17. The method of claim 16, wherein the effluents are conducted to the sample through a metallic or semi-metallic capillary tube.

* * * * *